United States Patent
Wang et al.

(10) Patent No.: US 10,772,858 B2
(45) Date of Patent: Sep. 15, 2020

(54) BENZHYDROL DERIVATIVES FOR THE MANAGEMENT OF CONDITIONS RELATED TO HYPOXIA INDUCIBLE FACTORS

(71) Applicants: GEORGIA STATE UNIVERSITY RESEARCH FOUNDATION, Atlanta, GA (US); Emory University, Atlanta, GA (US)

(72) Inventors: Binghe Wang, Marietta, GA (US); Erwin Van Meir, Tucker, GA (US); Jalisa Holmes Ferguson, Chamblee, GA (US); Stefan Kaluz, Atlanta, GA (US); Xingyue Ji, Atlanta, GA (US)

(73) Assignees: GEORGIA STATE UNIVERSITY RESEARCH FOUNDATION, INC., Atlanta, GA (US); EMORY UNIVERSITY, Atlanta, GA (US)

(*) Notice: Subject to any disclaimer, the term of this patent is extended or adjusted under 35 U.S.C. 154(b) by 0 days.

(21) Appl. No.: 15/570,969

(22) PCT Filed: May 2, 2016

(86) PCT No.: PCT/US2016/030451
§ 371 (c)(1),
(2) Date: Oct. 31, 2017

(87) PCT Pub. No.: WO2016/179108
PCT Pub. Date: Nov. 10, 2016

(65) Prior Publication Data
US 2018/0289664 A1    Oct. 11, 2018

Related U.S. Application Data

(60) Provisional application No. 62/155,501, filed on May 1, 2015.

(51) Int. Cl.
*A61K 31/192* (2006.01)
*A61K 31/495* (2006.01)
(Continued)

(52) U.S. Cl.
CPC ............ *A61K 31/192* (2013.01); *A01N 31/04* (2013.01); *A61K 31/085* (2013.01); *A61K 31/09* (2013.01);
(Continued)

(58) Field of Classification Search
CPC .......................... A61K 31/192; A61K 31/341
(Continued)

(56) References Cited

U.S. PATENT DOCUMENTS

| 5,719,306 A | 2/1998 | Chandrakumar et al. |
| 6,506,876 B1 | 1/2003 | Chandrakumar et al. |

(Continued)

FOREIGN PATENT DOCUMENTS

| CN | 102883607 A | 1/2013 |
| CN | 104302289 A | 1/2015 |

(Continued)

OTHER PUBLICATIONS

Anderson, Amy, Chem & Biol (2003), vol. 10, pp. 787-797. (Year: 2003).*

(Continued)

*Primary Examiner* — Craig D Ricci
*Assistant Examiner* — Janet L. Coppins
(74) *Attorney, Agent, or Firm* — Kilpatrick Townsend & Stockton LLP

(57) ABSTRACT

This disclosure relates to benzhydrol derivatives for managing conditions related to the Hypoxia Inducible Factor (HIF) pathway such as uses in treating cancer. In certain embodiment, the disclosure contemplates compounds and pharmaceutical compositions. In certain embodiment, the (Continued)

disclosure contemplates compounds disclosed herein as prodrugs, optionally substituted with one or more substituents, derivatives, or salts thereof.

10 Claims, 4 Drawing Sheets

(51) Int. Cl.
| | |
|---|---|
| A01N 31/04 | (2006.01) |
| A61K 31/7068 | (2006.01) |
| A61K 31/536 | (2006.01) |
| A61K 31/435 | (2006.01) |
| A61K 31/175 | (2006.01) |
| A61K 31/17 | (2006.01) |
| A61K 31/475 | (2006.01) |
| A61K 31/166 | (2006.01) |
| A61P 35/00 | (2006.01) |
| A61K 31/085 | (2006.01) |
| A61K 31/09 | (2006.01) |
| A61K 31/341 | (2006.01) |
| A61K 31/343 | (2006.01) |
| A61K 31/351 | (2006.01) |
| A61K 31/352 | (2006.01) |
| A61K 31/357 | (2006.01) |
| A61K 31/381 | (2006.01) |
| A61K 31/397 | (2006.01) |
| A61K 31/40 | (2006.01) |
| A61K 31/421 | (2006.01) |
| A61K 31/436 | (2006.01) |
| A61K 31/443 | (2006.01) |
| A61K 31/444 | (2006.01) |
| A61K 31/445 | (2006.01) |
| A61K 31/5375 | (2006.01) |
| A61K 31/538 | (2006.01) |
| A61K 45/06 | (2006.01) |
| C07C 43/295 | (2006.01) |
| C07D 205/04 | (2006.01) |
| C07D 207/12 | (2006.01) |
| C07D 211/46 | (2006.01) |
| C07D 213/65 | (2006.01) |
| C07D 263/32 | (2006.01) |
| C07D 265/36 | (2006.01) |
| C07D 295/096 | (2006.01) |
| C07D 307/12 | (2006.01) |
| C07D 307/20 | (2006.01) |
| C07D 307/79 | (2006.01) |
| C07D 309/10 | (2006.01) |
| C07D 311/70 | (2006.01) |
| C07D 319/16 | (2006.01) |
| C07D 333/54 | (2006.01) |
| C07D 405/12 | (2006.01) |
| C07D 491/052 | (2006.01) |

(52) U.S. Cl.
CPC .......... *A61K 31/166* (2013.01); *A61K 31/17* (2013.01); *A61K 31/175* (2013.01); *A61K 31/341* (2013.01); *A61K 31/343* (2013.01); *A61K 31/351* (2013.01); *A61K 31/352* (2013.01); *A61K 31/357* (2013.01); *A61K 31/381* (2013.01); *A61K 31/397* (2013.01); *A61K 31/40* (2013.01); *A61K 31/421* (2013.01); *A61K 31/436* (2013.01); *A61K 31/443* (2013.01); *A61K 31/444* (2013.01); *A61K 31/445* (2013.01); *A61K 31/475* (2013.01); *A61K 31/495* (2013.01); *A61K 31/536* (2013.01); *A61K 31/538* (2013.01); *A61K 31/5375* (2013.01); *A61K 31/7068* (2013.01); *A61K 45/06* (2013.01); *A61P 35/00* (2018.01); *C07C 43/295* (2013.01); *C07D 205/04* (2013.01); *C07D 207/12* (2013.01); *C07D 211/46* (2013.01); *C07D 213/65* (2013.01); *C07D 263/32* (2013.01); *C07D 265/36* (2013.01); *C07D 295/096* (2013.01); *C07D 307/12* (2013.01); *C07D 307/20* (2013.01); *C07D 307/79* (2013.01); *C07D 309/10* (2013.01); *C07D 311/70* (2013.01); *C07D 319/16* (2013.01); *C07D 333/54* (2013.01); *C07D 405/12* (2013.01); *C07D 491/052* (2013.01)

(58) Field of Classification Search
USPC .......................................... 514/646
See application file for complete search history.

(56) References Cited

U.S. PATENT DOCUMENTS

| 7,470,723 B2 | 12/2008 | Muller et al. |
| 2009/0054435 A1* | 2/2009 | Imoto ................ C07C 59/90 |
| | | 514/235.5 |
| 2010/0174074 A1 | 7/2010 | Kamal et al. |
| 2012/0022121 A1 | 1/2012 | Dalton et al. |
| 2013/0197049 A1 | 8/2013 | Li et al. |

FOREIGN PATENT DOCUMENTS

| EP | 2871187 A1 | 5/2015 | |
| WO | 93/23357 A1 | 11/1993 | |
| WO | 94/13291 A1 | 6/1994 | |
| WO | 2004/087644 A1 | 10/2004 | |
| WO | WO-2013106432 A1 * | 7/2013 | ........ A61K 31/415 |
| WO | 2014/007412 A1 | 1/2014 | |

OTHER PUBLICATIONS

Burroughs et al, Future Chem Med (2014), vol. 5(5), pp. 1-31. (Year: 2014).*
Thiel, Karl (2004), vol. 22(5), pp. 513-519. (Year: 2004).*
Alvarez et al., "Diarylmethyloxime and Hydrazone Derivatives With 5-indolyl Moieties as Potent Inhibitors of Tubulin Polymerization", Bioorganic & Medicinal Chemistry, vol. 16, No. 11, Jun. 1, 2008, pp. 5952-5961.
Alvarez et al., "Exploring the Effect of 2,3,4—Trimethoxy-phenyl Moiety as a Component of Indolephenstatins", European Journal of Medicinal Chemistry, vol. 45, No. 2, Feb. 2010, pp. 588-597.
Alvarez et al., "Isocombretastatins a: 1,1-diarylethenes as Potent Inhibitors of Tubulin Polymerization and Cytotoxic Compounds", Bioorganic & Medicinal Chemistry, vol. 17, No. 17, Sep. 1, 2009, pp. 6422-6431.
Alvarez et al., "Naphthylphenstatins as Tubulin Ligands: Synthesis and Biological Evaluation", Bioorganic & Medicinal Chemistry, vol. 16, No. 19, Oct. 1, 2008, pp. 8999-9008.
Chen et al., "Microwave-assisted Nickel (II) Acetylacetonatecatalyzed Arylation of Aldehydes With Arylboronic Acids", Tetrahedron Letters, vol. 52, No. 14, 2011, pp. 1677-1679.
Cleverdon et al., "514. The Dipole Moments of Some Derivatives of Diphenyl-Methanol and Related Compounds", Journal of the Chemical Society, Jan. 1, 1951, pp. 2321-2323.
Extended European Search Report issued in Application No. 16789902.0 dated Jan. 3, 2019.
Nasveschuk et al., "Discovery and Optimization of Tetramethylpiperidinyl Benzamides as Inhibitors of Ezh2", Acs Medicinal Chemistry Letters, vol. 5, No. 4, Jan. 23, 2014, pp. 378-383.

(56) References Cited

OTHER PUBLICATIONS

Pericherla et al., "Synthesis and Antiproliferative Activities of Quebecol and Its Analogs", Bioorganic & Medicinal Chemistry Letters, vol. 23, No. 19, 2013, pp. 5329-5331.
Poirot et al., "Synthesis, Binding and Structure-Affinity Studies of New Ligands for the Microsomal Anti-estrogen Binding Site", Bioorganic & Medicinal Chemistry, vol. 8, No. 8, Aug. 2000, pp. 2007-2016.
International Search Report and Written Opinion issued in Application No. PCT/US2016/030451 dated Aug. 9, 2016.
N-glycyl-5-o-phosphonopentofuranosylamine, Pubchem, (Oct. 24, 2012), Database accession No. 152.
Pentane-1,5-diamine, Pubchem, (Oct. 24, 2012), Database accession No. 273.
Pubchem CID 7111416, Bis(4-butoxy-3-methoxyphenyl)methanol, Create Date: Mar. 21, 2013, 12 pages.
Pubchem CID 65591273, (3,4-Dimethoxyphenyl)-[3-(methoxymethyl)phenyl]methanol, Create Date: Oct. 24, 2012, 10 pages.
Pubchem CID 65624152, (3,4-Dimethoxyphenyl)-[4-methoxymethyl)phenyl]methanol, Create Date: Oct. 24, 2012, 9 pages.
Chinese Patent Application No. 201680034730.0, First Office Action dated Nov. 1, 2019, along with an English translation, 21 pages.
CN201680034730.0, "Office Action", dated Jun. 8, 2020, 11 pages (20 pages with English Translation).

\* cited by examiner

BENZHYDROL DERIVATIVES FOR THE MANAGEMENT OF CONDITIONS RELATED TO HYPOXIA INDUCIBLE FACTORS

STATEMENT REGARDING FEDERALLY FUNDED RESEARCH

This invention was made with government support under Grants CA116804 and CA180805 awarded by the National Institutes of Health. The government has certain rights in the invention.

BACKGROUND

Effective treatments for cancer are a major challenge among researchers and there is a need for new therapies targeting abnormal proliferative disorders. The presence of hypoxic areas in solid cancers has been correlated with resistance to chemotherapy and radiation treatment. Hypoxia inducible factors (HIFs) are transcription factors that activate genes controlling mechanisms such as glycolysis, erythropoiesis, angiogenesis, epithelial to mesenchymal transition, and cell motility and invasion/metastasis, which can benefit the survival of cancer cells. HIFs are heterodimeric protein complexes, composed of HIF1-α and HIF1-β subunits, which then associate with cofactors such as p300 and CBP to form active transcription factors. The regulation of HIFs largely occurs at the protein level, and is dependent upon the synthesis and stability of the HIF1-α subunits. Under normoxia, HIF1-α subunits are hydroxylated at proline residues by oxygen-dependent prolyl hydroxylases (PHDs), which mediates recognition by the Von Hippel-Lindau (VHL) E3 ubiquitin ligase complex and rapid degradation by the proteasome. Under hypoxia, HIF1-α subunits are stabilized due to the inhibition of proline hydroxylation, and a functional HIF transcriptional complex is assembled, translocates to the nucleus, and transcribes genes that contain DNA sequences called hypoxia response elements (HREs). Elevated levels of HIF-1α have been correlated with poor prognosis of patients with cancers.

Tumor cells overexpressing HIFs represent an important target for antitumor therapy. Zhang et al. report digoxin and other cardiac glycosides inhibit HIF-1 alpha synthesis and block tumor growth. PNAS, 2008, 105(50):19579-19586. A number of existing chemotherapeutics can alter HIF activity including 2ME2, 17-DMAG, 17-AAG, camptothecin, PX-478, and YC-1. Ellinghaus et al. report that BAY 87-2243 inhibits HIF-1α Cancer Medicine, 2013, 2(5): 611-624. Antitumor activity of BAY 87-2243 in vivo was demonstrated in a H460 xenograft model. BAY 87-2243 also inhibits mitochondrial complex I activity. Interference with mitochondrial function to reduce hypoxia-induced HIF-1 activity in tumors is indicated as a therapeutic approach to overcome chemo- and radiotherapy resistance of hypoxic tumors.

A number of patent applications report small molecules for use in the treatment of hypoxia related pathologies (see e.g. US Published Application 2013-0164218, WO 2004/087066, WO 2007/025169, WO 2010/006184, and WO 2010/006189). See also Sato et al., 2000, Proc Natl Acad Sci USA, 97:10832-10837; Whitesell et al., 1994, Proc Natl Acad Sci USA., 91:8324-8328; Zhou et al. 2004, J. Biol. Chem. 279:13506-13513; Katschinski et al., 2002, J. Biol. Chem. 277:9262-9267 and Isaacs et al., 2002, J Biol Chem., 277:29936-44).

References cited herein are not an admission of prior art.

SUMMARY

This disclosure relates to benzhydrol derivatives for managing conditions related to the Hypoxia Inducible Factor (HIF) pathway such as uses in treating cancer. In certain embodiments, the disclosure contemplates compounds disclosed herein as prodrugs, optionally substituted with one or more substituents, derivatives, or salts thereof. In certain embodiments, the benzhydrol derivatives have Formula I,

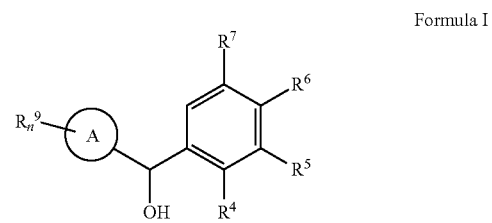

Formula I wherein substituents are described herein.

In certain embodiments, the disclosure contemplates compounds and pharmaceutical compositions. In certain embodiments, the disclosure relates to pharmaceutical compositions comprising a compound disclosed herein or a pharmaceutically acceptable salt and a pharmaceutically acceptable excipient.

In certain embodiments, the pharmaceutical composition is in the form of a pill, tablet, capsule, or gel and optionally a layer of polymeric material enveloping the form. In certain embodiments, the compound is a particle form of a size between 5 nanometers and 1 mm or 1 cm optionally having a layer of polymeric material enveloping the particles. In certain embodiments, the compound is in the form of an aqueous solution further comprising a buffering agent, oil, phosphate buffer, sodium or potassium salt, a saccharide, polysaccharide, or solubilizing agent.

In certain embodiments, the disclosure relates to methods of treating cancer comprising administering an effective amount of a pharmaceutical composition comprising a compound disclosed herein to a subject in need thereof. In certain embodiments, the cancer is selected from glioblastoma (GBM), breast, pancreatic, colon, metastatic lung cancers, bladder cancer, lung cancer, eye cancer, melanoma, colon and rectal cancer, non-Hodgkin lymphoma, endometrial cancer, pancreatic cancer, kidney cancer, prostate cancer, leukemia, thyroid cancer, and brain cancer.

In certain embodiments, the composition is administered in combination with a second anti-cancer agent such as temozolomide, carmustine, bevacizumab, procarbazine, lomustine, vincristine, gefitinib, erlotinib, docetaxel, cisplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, taxol, docetaxel, etoposide, tenipo-side, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, and/or lenalidomide or combinations thereof.

In certain embodiments, the composition is administered in combination with a matrix, e.g., biodegradable polymer loaded with the chemotherapeutic agent, e.g., gliadel wafers which contain carmustine. In certain embodiments, the polymer is designed to release this agent over a two, three, or more week period. The polymers are implanted in resected tumor beds and after initial resection.

In certain embodiments, the disclosure relates to methods of preventing pests from eating a plant comprising contacting a plant with a compound disclosed herein with mitochondrial complex I inhibition properties thereby preventing the pest from eating the plant.

In certain embodiments, the disclosure relates to methods of preventing pests from living in the skin or hair of a subject comprising contacting skin or hair of the subject with a compound disclosed herein with mitochondrial complex I inhibition properties in an effective manner to a subject at risk of, suspected of, exhibiting symptoms of, or diagnosed with a pest living on the subject.

DETAILED DISCUSSION

Figure 1:
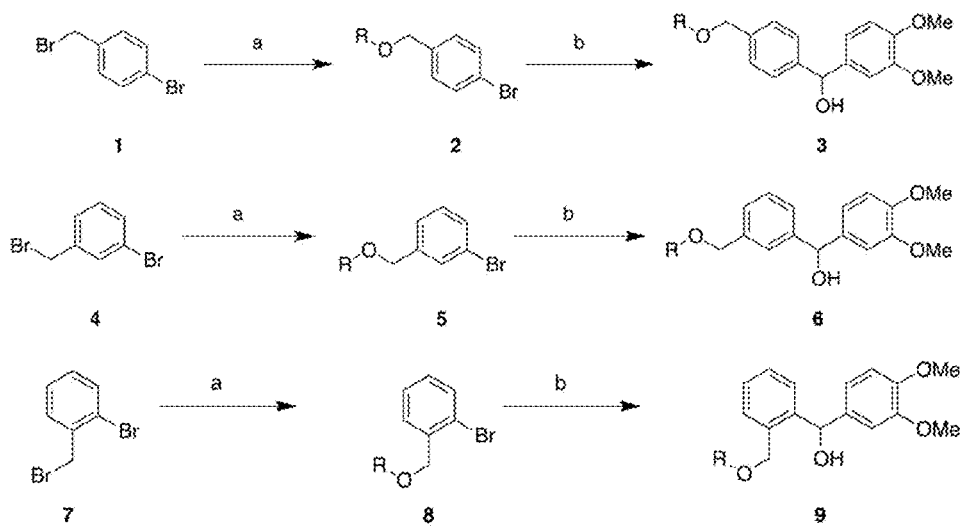
FIG. 1 illustrates the preparation of certain embodiments of the disclosure. Para substituted compounds were synthesized in 2 steps from commercially available 1-bromo-4-(bromomethyl)benzene 1 (FIG. 1). First, 1 underwent $S_N2$ displacement with corresponding alcohols to yield ethers 2a-w. Next, after lithiation, 2a-w were reacted with the appropriate aldehyde to yield alcohol compounds 3a-w. Reagents and conditions: (a) NaH, alcohol, 0° C. to room temperature, overnight, 48-85%; b) n-BuL$_1$, aldehyde, −78° C., 58-94%. Meta and ortho substituted substituents were prepared using the corresponding commercially available starting materials, e.g., 1-bromo-3-(bromomethyl)benzene and 1-bromo-2-(bromomethyl)benzene.
Figure 2:
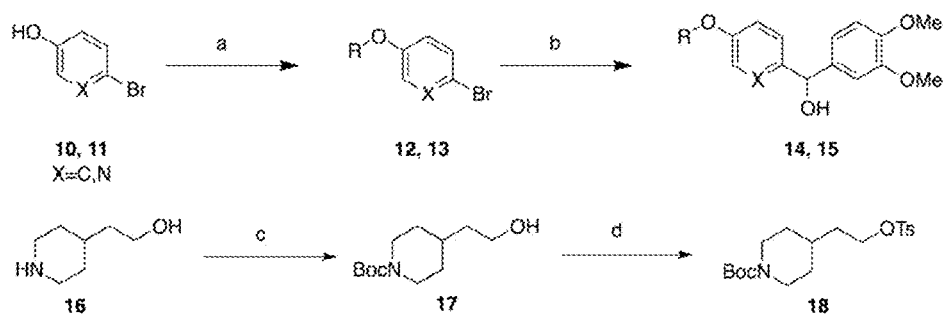
FIG. 2 illustrates the preparation of certain embodiments of the disclosure. 13a, b, d-j were synthesized in two steps by an $S_N2$ reaction with 4-bromophenol, 10, or 2-bromo-5-hydroxypyridine, 11, followed by lithium halogen exchange to yield ethers 12a, b, d; 13a-d and alcohols 14a, b, d; 15a-d, respectively. For compound 14c, N-Boc protection of tert-butyl 4-(2-hydroxyethyl)piperidine-1-carboxylate 16 was required before O-tosylation of 17 to yield intermediate 18. At that point, the tosyl group was displaced by 4-bromophenol in an $S_N2$ reaction to yield ether 12c followed by coupling with 3,4-dimethoxybenzaldehyde to yield alcohol compound 14c.
Figure 3:
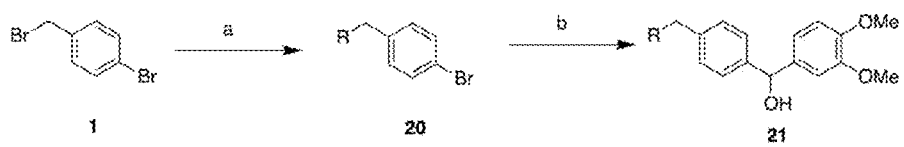
FIG. 3 illustrates the preparation of certain embodiments of the disclosure. 1-Bromo-4-(bromomethyl)benzene, 1, underwent $S_N2$ displacement with morpholine, or N-methyl piperazine to yield compounds 20a-b. Next, 20a-c were reacted with n-butyllithium and then 3,4-dimethoxybenzaldehyde to yield alcohols 21a-c. Reagents and conditions: (a) amine, $K_2CO_3$, acetonitrile, room temperature. (b) 3,4-dimethoxy benzaldehyde, n-BuLi, −78° C., 85%. (c) 3,4-dimethoxybromobenzenee, n-BuLi, −78° C., 89%.
Figure 4:
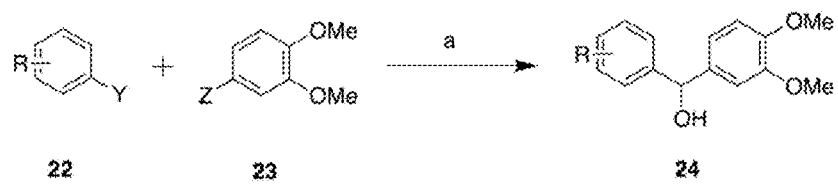
FIG. 4 illustrates the preparation of certain embodiments of the disclosure. Compounds were synthesized in 1 step from commercially available starting materials 22a-f and 23, which consist of an aryl bromide and an aryl aldehyde, which were coupled together to yield alcohols 24a-f, wherein R═H, Y═Br, Z═CHO, 24a; R=3,4-dimethoxy, Y═Br, Z═CHO, 24b; R=2,4-dimethoxy, Y═Br, Z═CHO, 24c; R=4-methylbromide, Y═Br, Z═CHO, 24d; R=benzofuran, Y═CHO, Z═Br, 24e. Reagents and conditions: (a) n-BuLi, −78° C., 46-65%.
Figure 5:
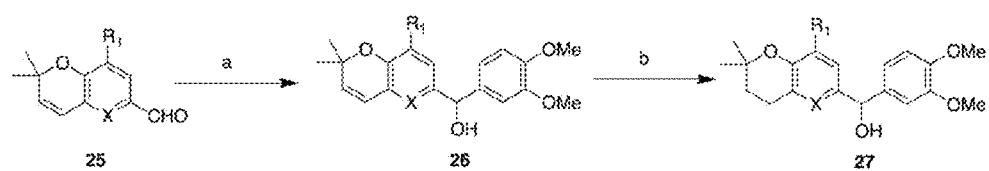
FIG. 5 illustrates the preparation of certain embodiments of the disclosure. Compounds were synthesized in 1 or 2 steps from readily synthesized aldehydes 25a, c, and d. First, aldehydes 25a, c, and d were coupled with 4-bromo-1,2-dimethoxybenzene through lithiation and then addition reaction to yield alcohols 26a-d. Next, the double bond was hydrogenated to a single bond to yield compounds 27c and 27d. R1=H, X═C, 25-26a and b; R1=OMe, X═C, 25-27c; R1=H, X═N, 25-27d; Reagents and conditions: (a) 4-bromo-1,2-dimethoxybenzene, n-BuLi, −78° C., 49-63%; (b) $H_2$, Pd/C, MeOH, overnight.
Figure 6:
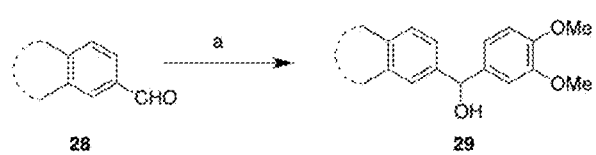
FIG. 6 illustrates the preparation of certain embodiments of the disclosure. Compounds 29a-d were synthesized in one step from readily synthesized aldehydes 28a-d. First, aldehydes 28a-d were coupled with 4-bromo-1,2-dimethoxybenzene through lithiation and then addition reaction to yield alcohols 29a-d. 2,3-dihydrobenzofuran-5-yl, 28-29a; (4-methyl-3,4-dihydro-2H-benzo[b][1,4]oxazin-7-yl), 28-29b; naphthalen-2-yl, 28-29c; (2,3-dihydro benzo[b][1,4]dioxin-6-yl), 28-29d; (2-methylbenzo[b]thiophen-5-yl), 28-29e and f. Reagents and Conditions: (a) 4-bromo-1,2-dimethoxybenzene, n-BuLi, −78° C., 49-63%.
Figure 7:
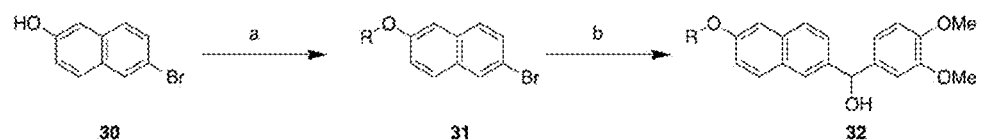
FIG. 7 illustrates the preparation of certain embodiments of the disclosure. Compounds 32a-d were synthesized in two steps by an $S_N2$ reaction with corresponding alcohols and 6-bromonaphthalen-2-ol, 30, followed by lithium halogen exchange to yield ethers 31a-d and alcohols 32a-d, respectively.
Figure 8:
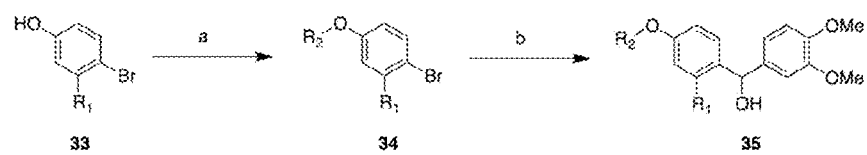
FIG. 8 illustrates the preparation of certain embodiments of the disclosure. Compounds were synthesized in two steps from substituted bromophenols 33a-c and corresponding alkyl bromides. R1=methoxy, R2=3-hydroxytetrahydrofuryl, 33-35a; R1=fluoro, R2=n-pentyl, 33-35b; R1=methyl, R2=n-pentyl, 33-35c; R1=methyl, R2=tert-butyl 4-(oxymethyl)piperidine-1-carboxylate, 33-35d; R1=methyl, R2=tert-butyl 4-(oxymethyl)piperidine-1-carboxylate, 33-35e; R1=methyl, R2=tert-butyl 4-(oxymethyl)piperidine-1-carboxylate, 33-35f. Reagents and conditions: (a) $K_2CO_3$, acetonitrile, reflux; (b) 4-bromo-1,2-dimethoxybenzene, n-BuLi, −78° C.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers to an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

"Aminoalkyl" refers to an amino group attached through an alkyl bridge. An example of an aminoalkyl is aminomethyl, (i.e., $NH_2$—$CH_2$—).

"Hydroxyalkyl" refers to a hydroxy group attached through an alkyl bridge. An example of a hydroxyalkyl is hydroxyethyl, (i.e., HO—$CH_2CH_2$—).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO₂Rb, —C(=O)Ra, —C(=O)ORa, —C(=O)NRaRb, —OC(=O)NRaRb, —ORa, —SRa, —SORa, —S(=O)₂Ra, —OS(=O)₂Ra and —S(=O)₂ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers to any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Benzhydrol Derivatives

In certain embodiments, the disclosure contemplates benzhydrol derivatives of Formula I for any of the uses reported herein. Compounds of Formula I may be

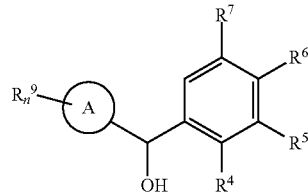

Formula I prodrugs or salts thereof wherein,

A is a carbocyclyl, aryl, phenyl, benzyl, or heterocyclyl ring having n is 0, 1, 2, or 3, $R^9$ substituents;

$R^4$, $R^5$, $R^6$, $R^7$, and $R^9$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkylsulfonyl, arylsulfonyl, carbocyclyl, aryl, or heterocyclyl, wherein $R^4$, $R^5$, $R^6$, $R^7$, and $R^9$ are optionally substituted with one or more, the same or different, $R^{20}$;

$R^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^6$ is alkoxy or $R^5$ and $R^6$ are alkoxy.

In certain embodiments, A is phenyl.

In certain embodiments, A is benz-4-yl, or benz-3-yl ring.

In certain embodiments, $R^9$ is alkoxy optionally substituted.

In certain embodiments, $R^9$ is hydroxyalkyl, optionally substituted.

In certain embodiments, $R^9$ is ((piperidin-4-yl)oxy)methyl or (((N-alkoxycarbonyl)piperidin-4-yl)oxy)methyl.

In certain embodiments, $R^9$ is (2-piperidin-4-yl)ethoxy or (2-(N-alkoxycarbonyl)piperidin-4-yl)ethoxy.

In certain embodiments, derivatives of Formula I have Formula IA,

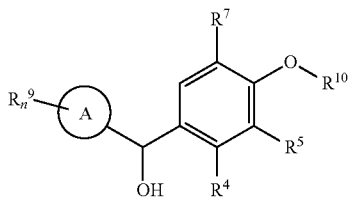

Formula IA prodrugs or salts thereof wherein,

A is a carbocyclyl, aryl, phenyl, benzyl, or heterocyclyl ring having n is 0, 1, 2, or 3, $R^9$ substituents;

$R^4$, $R^5$, $R^7$, and $R^9$ are the same as defined herein above;

$R^{10}$ is alkyl, formyl, alkanoyl, carbamoyl, hydroxyalkyl, aminoalkyl, or thioalkyl wherein $R^{10}$ is optionally substituted with one or more, the same or different, $R^{20}$;

$R^{20}$ and $R^{21}$ are the same as defined herein above.

In certain embodiments, $R^5$ is alkoxy.

In certain embodiments, A is phenyl.

In certain embodiments, A is benz-4-yl, or benz-3-yl ring.

In certain embodiments, $R^9$ is alkoxy optionally substituted.

In certain embodiments, $R^9$ is hydroxyalkyl, optionally substituted.

In certain embodiments, $R^9$ is ((piperidin-4-yl)oxy)methyl or (((N-alkoxycarbonyl)piperidin-4-yl)oxy)methyl.

In certain embodiments, $R^9$ is (2-piperidin-4-yl)ethoxy or (2-(N-alkoxycarbonyl)piperidin-4-yl)ethoxy.

In certain embodiments, derivatives of Formula I have Formula IB,

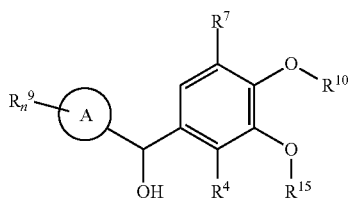

Formula IB prodrugs or salts thereof wherein,

A is a carbocyclyl, aryl, phenyl, benzyl, or heterocyclyl ring having n is 0, 1, 2, or 3, $R^9$ substituents;

$R^4$, $R^7$, and $R^9$ are the same as defined herein above;

$R^{10}$ is alkyl, formyl, alkanoyl, carbamoyl, hydroxyalkyl, aminoalkyl, or thioalkyl wherein $R^{10}$ is optionally substituted with one or more, the same or different, $R^{20}$;

$R^{15}$ is alkyl, formyl, alkanoyl, carbamoyl, hydroxyalkyl, aminoalkyl, or thioalkyl wherein $R^{15}$ is optionally substituted with one or more, the same or different, $R^{20}$;

$R^{20}$ and $R^{21}$ are the same as defined herein above.

In certain embodiments, A is phenyl.

In certain embodiments, A is benz-4-yl, or benz-3-yl ring.

In certain embodiments, $R^9$ is alkoxy optionally substituted.

In certain embodiments, $R^9$ is hydroxyalkyl, optionally substituted.

In certain embodiments, $R^9$ is ((piperidin-4-yl)oxy)methyl or (((N-alkoxycarbonyl)piperidin-4-yl)oxy)methyl.

In certain embodiments, $R^9$ is (2-piperidin-4-yl)ethoxy or (2-(N-alkoxycarbonyl)piperidin-4-yl)ethoxy.

In certain embodiments, derivatives of Formula I have Formula IC,

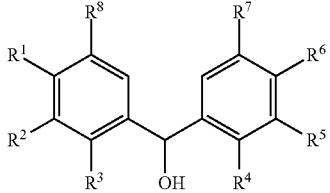

Formula IC prodrugs or salts thereof wherein, $R^1$ is hydrogen, hydroxyalkyl, or alkoxy wherein $R^1$ is optionally substituted with one or more, the same or different, $R^{20}$ and $R^2$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^2$ is optionally substituted with one or more, the same or different, $R^{20}$; or $R^1$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^1$ is optionally substituted with one or more, the same or different, $R^{20}$, and $R^2$ is hydrogen, hydroxyalkyl, or alkoxy wherein $R^2$ is optionally substituted with one or more, the same or different, $R^{20}$;

$R^3$, $R^4$, $R^5$, $R^7$, and $R^8$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^3$, $R^4$, $R^5$, $R^7$, and $R^8$ are optionally substituted with one or more, the same or different, $R^{20}$;

$R^6$ is alkoxy optionally substituted with one or more, the same or different, $R^{20}$;

$R^{20}$ and $R^{21}$ are the same as defined herein above.

In certain embodiments, $R^3$ is alkyl.

In certain embodiments, $R^6$ is alkoxy or $R^5$ and $R^6$ are alkoxy.

In certain embodiments, $R^1$ or $R^2$ is alkoxy optionally substituted.

In certain embodiments, $R^1$ or $R^2$ is hydroxyalkyl, optionally substituted.

In certain embodiments, $R^1$ or $R^2$ is ((piperidin-4-yl)oxy)methyl or (((N-alkoxycarbonyl)piperidin-4-yl)oxy)methyl.

In certain embodiments, $R^1$ or $R^2$ is (2-piperidin-4-yl)ethoxy or (2-(N-alkoxycarbonyl)piperidin-4-yl)ethoxy.

In certain embodiments, derivatives of Formula I have Formula ID,

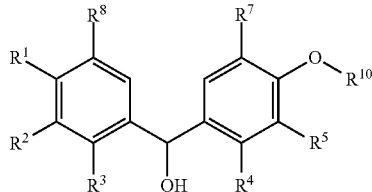

Formula ID prodrugs or salts thereof wherein,
$R^1$, $R^2$, $R^3$, $R^4$, $R^5$, $R^7$, $R^8$, $R^{10}$, $R^{20}$ and $R^{21}$ are the same as defined herein above.

In certain embodiments, $R^3$ is alkyl.
In certain embodiments, $R^5$ is alkoxy.
In certain embodiments, $R^1$ or $R^2$ is alkoxy optionally substituted.
In certain embodiments, $R^1$ or $R^2$ is hydroxyalkyl, optionally substituted.
In certain embodiments, $R^1$ or $R^2$ is ((piperidin-4-yl)oxy)methyl or (((N-alkoxycarbonyl)piperidin-4-yl)oxy)methyl.
In certain embodiments, $R^1$ or $R^2$ is (2-piperidin-4-yl)ethoxy or (2-(N-alkoxycarbonyl)piperidin-4-yl)ethoxy.

In certain embodiments, derivatives of Formula I have Formula IE,

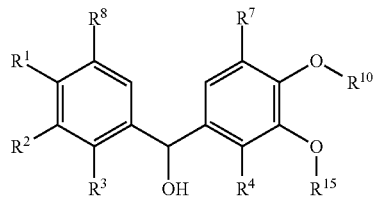

Formula IE prodrugs or salts thereof wherein,
$R^1$, $R^2$, $R^3$, $R^4$, $R^5$, $R^7$, $R^8$, $R^{10}$, $R^{15}$, $R^{20}$ and $R^{21}$ are the same as defined herein above.

In certain embodiments, $R^3$ is alkyl.
In certain embodiments, $R^1$ or $R^2$ is alkoxy optionally substituted.
In certain embodiments, $R^1$ or $R^2$ is hydroxyalkyl, optionally substituted.
In certain embodiments, $R^1$ or $R^2$ is ((piperidin-4-yl)oxy)methyl or (((N-alkoxycarbonyl)piperidin-4-yl)oxy)methyl.
In certain embodiments, $R^1$ or $R^2$ is (2-piperidin-4-yl)ethoxy or (2-(N-alkoxycarbonyl)piperidin-4-yl)ethoxy.

In certain embodiments, derivatives of Formula I have Formula IF,

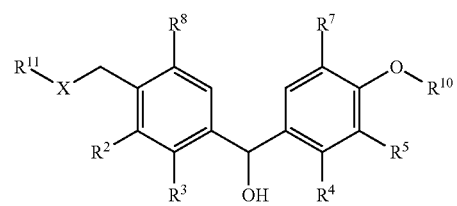

Formula IF prodrugs or salts thereof wherein,
X is the bridging group —O—, —S—, —NH—, —N-alkyl-, C=O, —CH$_2$—, —CH$_2$O—, —CH$_2$S—, —CH$_2$NH—, —CH$_2$(C=O)—, —CH$_2$CH$_2$—, —CH$_2$CH$_2$O—, —CH$_2$CH$_2$S—, —CH$_2$CH$_2$NH—, —CH$_2$CH$_2$Nalkyl-, —CH$_2$CH$_2$(C=O)—, —CH$_2$CH$_2$CH$_2$—, or single bond between benzyl and $R^{11}$;
$R^{11}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^{11}$ is optionally substituted with one or more, the same or different, $R^{20}$;
$R^2$, $R^3$, $R^4$, $R^5$, $R^7$, $R^8$, $R^{10}$, $R^{20}$ and $R^{21}$ are the same as defined herein above.

In certain embodiments, $R^3$ is alkyl.
In certain embodiments, X is —CH$_2$CH$_2$O—
In certain embodiments, $R^{11}$ is a heterocyclyl.

In certain embodiments, derivatives of Formula I have Formula IG,

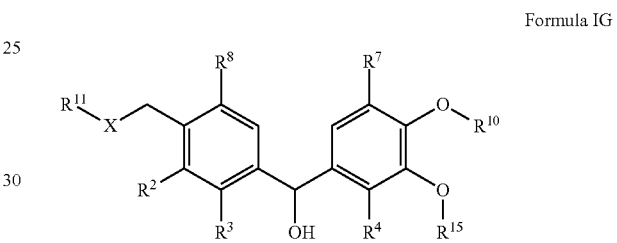

Formula IG prodrugs or salts thereof wherein,
X is the bridging group —O—, —S—, —NH—, —N-alkyl-, C=O, —CH$_2$—, —CH$_2$O—, —CH$_2$S—, —CH$_2$NH—, —CH$_2$(C=O)—, —CH$_2$CH$_2$—, —CH$_2$CH$_2$O—, —CH$_2$CH$_2$S—, —CH$_2$CH$_2$NH—, —CH$_2$CH$_2$Nalkyl-, —CH$_2$CH$_2$(C=O)—, —CH$_2$CH$_2$CH$_2$—, or single bond between benzyl and $R^{11}$;
$R^{11}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^{11}$ is optionally substituted with one or more, the same or different, $R^{20}$;
$R^2$, $R^3$, $R^4$, $R^7$, $R^8$, $R^{10}$, $R^{15}$, $R^{20}$ and $R^{21}$ are the same as defined herein above.

In certain embodiments, $R^3$ is alkyl.
In certain embodiments, X is —CH$_2$CH$_2$O—
In certain embodiments, $R^{11}$ is a heterocyclyl.

In certain embodiments, derivatives of Formula I have Formula IH,

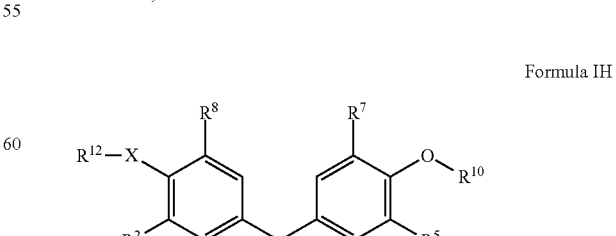

Formula IH prodrugs or salts thereof wherein,

X is the bridging group —O—, —S—, —NH—, —N-alkyl-, C=O, —CH$_2$—, —CH$_2$O—, —CH$_2$S—, —CH$_2$NH—, —CH$_2$(C=O)—, —CH$_2$CH$_2$—, —CH$_2$CH$_2$O—, —CH$_2$CH$_2$S—, —CH$_2$CH$_2$NH—, —CH$_2$CH$_2$Nalkyl-, —CH$_2$CH$_2$(C=O)—, —CH$_2$CH$_2$CH$_2$—, or single bond between phenyl and R$^{12}$;

R$^{12}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{12}$ is optionally substituted with one or more, the same or different, R$^{20}$;

R$^2$, R$^3$, R$^4$, R$^5$, R$^7$, R$^8$, R$^{10}$, R$^{20}$ and R$^{21}$ are the same as defined herein above.

In certain embodiments, R$^3$ is alkyl.

In certain embodiments, X is —CH$_2$CH$_2$O—

In certain embodiments, R$^{12}$ is a heterocyclyl.

In certain embodiments, derivatives of Formula I have Formula II,

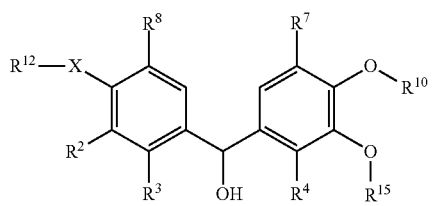

Formula II prodrugs or salts thereof wherein,

X is the bridging group —O—, —S—, —NH—, —N-alkyl-, C=O, —CH$_2$—, —CH$_2$O—, —CH$_2$S—, —CH$_2$NH—, —CH$_2$(C=O)—, —CH$_2$CH$_2$—, —CH$_2$CH$_2$O—, —CH$_2$CH$_2$S—, —CH$_2$CH$_2$NH—, —CH$_2$CH$_2$Nalkyl-, —CH$_2$CH$_2$(C=O)—, —CH$_2$CH$_2$CH$_2$—, or single bond between phenyl and R$^{12}$;

R$^2$, R$^3$, R$^4$, R$^7$, R$^8$, R$^{10}$, R$^{12}$, R$^{15}$, R$^{20}$ and R$^{21}$ are the same as defined herein above.

In certain embodiments, R$^3$ is alkyl.

In certain embodiments, X is —CH$_2$CH$_2$O—

In certain embodiments, R$^{12}$ is a heterocyclyl.

In certain embodiments, derivatives of Formula I have Formula IJ,

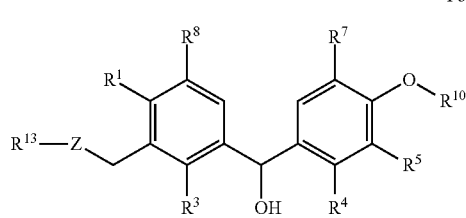

Formula IJ prodrugs or salts thereof wherein,

Z is the bridging group —O—, —S—, —NH—, —N-alkyl-, C=O, —CH$_2$—, —CH$_2$O—, —CH$_2$S—, —CH$_2$NH—, —CH$_2$(C=O)—, —CH$_2$CH$_2$—, —CH$_2$CH$_2$O—, —CH$_2$CH$_2$S—, —CH$_2$CH$_2$NH—, —CH$_2$CH$_2$Nalkyl-, —CH$_2$CH$_2$(C=O)—, —CH$_2$CH$_2$CH$_2$—, or single bond between benzyl and R$^{13}$;

R$^{13}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{13}$ is optionally substituted with one or more, the same or different, R$^{20}$;

R$^2$, R$^3$, R$^4$, R$^7$, R$^8$, R$^{10}$, R$^{15}$, R$^{20}$ and R$^{21}$ are the same as defined herein above.

In certain embodiments, Z is —O—.

In certain embodiments, R$^{14}$ is a heterocyclyl.

In certain embodiments, derivatives of Formula I have Formula IK,

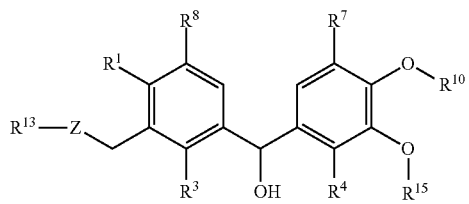

Formula IK prodrugs or salts thereof wherein,

Z is the bridging group —O—, —S—, —NH—, —N-alkyl-, C=O, —CH$_2$—, —CH$_2$O—, —CH$_2$S—, —CH$_2$NH—, —CH$_2$(C=O)—, —CH$_2$CH$_2$—, —CH$_2$CH$_2$O—, —CH$_2$CH$_2$S—, —CH$_2$CH$_2$NH—, —CH$_2$CH$_2$Nalkyl-, —CH$_2$CH$_2$(C=O)—, —CH$_2$CH$_2$CH$_2$—, or single bond between benzyl and R$^{13}$;

R$^{13}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{13}$ is optionally substituted with one or more, the same or different, R$^{20}$;

R$^1$, R$^3$, R$^4$, R$^7$, R$^8$, R$^{10}$, R$^{13}$, R$^{15}$, R$^{20}$ and R$^{21}$ are the same as defined herein above.

In certain embodiments, Z is —O—.

In certain embodiments, R$^{14}$ is a heterocyclyl.

In certain embodiments, derivatives of Formula I have Formula IL,

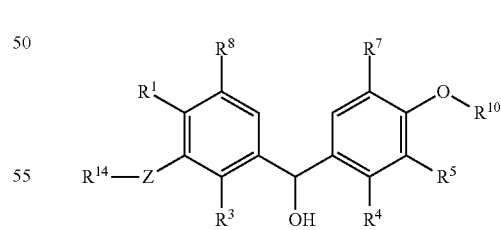

Formula IL prodrugs or salts thereof wherein,

Z is the bridging group —O—, —S—, —NH—, —N-alkyl-, C=O, —CH$_2$—, —CH$_2$O—, —CH$_2$S—, —CH$_2$NH—, —CH$_2$(C=O)—, —CH$_2$CH$_2$—, —CH$_2$CH$_2$O—, —CH$_2$CH$_2$S—, —CH$_2$CH$_2$NH—, —CH$_2$CH$_2$Nalkyl-, —CH$_2$CH$_2$(C=O)—, —CH$_2$CH$_2$CH$_2$—, or single bond between phenyl and R$^{14}$;

R$^{14}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{14}$ is optionally substituted with one or more, the same or different, R$^{20}$;

R$^1$, R$^3$, R$^4$, R$^5$, R$^7$, R$^8$, R$^{10}$, R$^{20}$ and R$^{21}$ are the same as defined herein above.

In certain embodiments, Z is —O—.

In certain embodiments, R$^{14}$ is a heterocyclyl.

In certain embodiments, derivatives of Formula I have Formula IM,

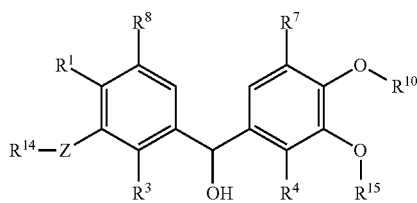

Formula IM prodrugs or salts thereof wherein,

Z is the bridging group —O—, —S—, —NH—, —N-alkyl-, C═O, —CH$_2$—, —CH$_2$O—, —CH$_2$S—, —CH$_2$NH—, —CH$_2$(C═O)—, —CH$_2$CH$_2$—, —CH$_2$CH$_2$O—, —CH$_2$CH$_2$S—, —CH$_2$CH$_2$NH—, —CH$_2$CH$_2$Nalkyl-, —CH$_2$CH$_2$(C═O)—, —CH$_2$CH$_2$CH$_2$—, or single bond between phenyl and R$^{14}$;

R$^{14}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{14}$ is optionally substituted with one or more, the same or different, R$^{20}$;

R$^1$, R$^3$, R$^4$, R$^7$, R$^8$, R$^{10}$, R$^{14}$, R$^{15}$, R$^{20}$ and R$^{21}$ are the same as defined herein above.

In certain embodiments, Z is —O—.

In certain embodiments, R$^{14}$ is a heterocyclyl.

In certain embodiments, derivatives of Formula I have Formula IM,

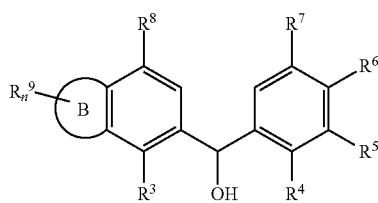

Formula IN prodrugs or salts thereof wherein,

B is a carbocyclyl, aryl, or heterocyclyl ring having n is 0, 1, 2, or 3, R$^9$ substituents;

R$^3$, R$^4$, R$^7$, R$^8$, R$^{20}$ and R$^{21}$ are the same as defined above.

R$^9$ is independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, arylsulfonyl, carbocyclyl, aryl, or heterocyclyl, wherein R$^9$ is optionally substituted with one or more, the same or different, R$^{20}$;

R$^6$ is alkoxy optionally substituted with one or more, the same or different, R$^{20}$;

are the same as defined herein above.

In certain embodiments, derivatives of Formula I have Formula IO,

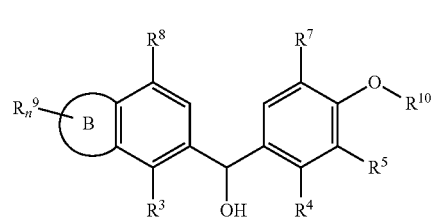

Formula IO prodrugs or salts thereof wherein,

B is a carbocyclyl, aryl, or heterocyclyl ring having n is 0, 1, 2, or 3, R$^9$ substituents;

R$^3$, R$^4$, R$^5$, R$^7$, R$^8$, R$^9$, R$^{10}$, R$^{20}$ and R$^{21}$ are the same as defined herein above.

In certain embodiments, derivatives of Formula I have Formula IP,

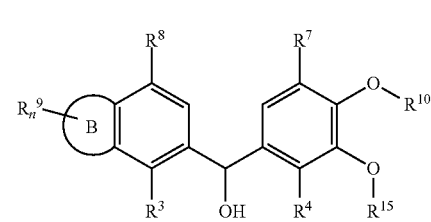

Formula IP prodrugs or salts thereof wherein,

B is a carbocyclyl, aryl, or heterocyclyl ring having n is 0, 1, 2, or 3, R$^9$ substituents;

R$^3$, R$^4$, R$^7$, R$^8$, R$^9$, R$^{10}$, R$^{15}$, R$^{20}$ and R$^{21}$ are the same as defined herein above.

In certain embodiments, derivatives of Formula I have Formula IQ,

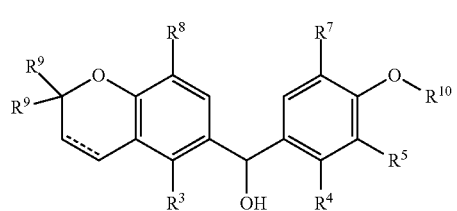

Formula IQ prodrugs or salts thereof wherein, the dotted line is a single bond or a double bond;

R$^3$, R$^4$, R$^5$, R$^7$, R$^8$, R$^9$, R$^{10}$, R$^{20}$ and R$^{21}$ are the same as defined herein above.

In certain embodiments, derivatives of Formula I have Formula IQ,

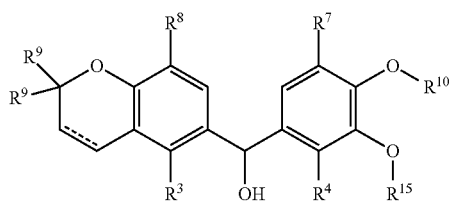

Formula IR prodrugs or salts thereof wherein,
the dotted line is a single bond or a double bond;
$R^3$, $R^4$, $R^7$, $R^8$, $R^9$, $R^{10}$, $R^{15}$, $R^{20}$ and $R^{21}$ are the same as defined herein above.

Managing Cancer

Hypoxia is a condition prevalent in solid tumor development. It has also been found in the bone marrow that produces "blood cancer" cells. To counter the detrimental effects, tumor cells activate a range of adaptive molecular mechanisms. Hypoxia-inducible factors (HIF) regulate the primary transcriptional response to hypoxia. HIFs consist of one of HIF-1α, 2α, or 3α (the O2-regulated subunits) and the constitutively expressed HIF-1β. Under normoxic conditions, α subunits are hydroxylated by a family of prolyl-hydroxylases, ubiquitinated in a Von Hippel-Lindau protein-dependent manner, and degraded in the proteasome. Under hypoxic conditions, α subunits are stabilized, translocate into the nucleus where they interact with the HIF-1β subunit, recruit co-activators p300/CBP, and regulate target genes via binding to specific DNA sequences termed hypoxia-responsive elements (HRE).

CBP and p300 are homologous transcriptional coactivators. The interaction between HIF-1α and p300/CBP is physiologically regulated via $O_2$-dependent hydroxylation of the C-terminal transactivation domain of HIF-1α by asparaginyl hydroxylase (FIH-1). Hydroxylation of asparagine 803 prevents binding of p300 or CBP and inhibits HIF-1 function in transcription. The important role of p300/CBP in HIF function has been established by showing that blockade of the HIF-1α-p300/CBP interaction markedly attenuated HIF activity.

The close relation of HIF-activated gene products with tumor progression/metastasis identifies HIF as an attractive therapeutic target. Previous studies have established that inhibition of the HIF pathway can inhibit malignant characteristics in a number of cancers. See Ryan et al., HIF-1 alpha is required for solid tumor formation and embryonic vascularization. EMBO J, 1998, 17:3005-15. See also Li et al. Cancer Res, 2005, 65:7249-58.

In a typical embodiment, the disclosure relates to a method treating or preventing cancer comprising administering to a patient a compound disclosed herein having HIF inhibitory activity. In some embodiments, the disclosure relates to a compound disclosed herein, or a pharmaceutically acceptable salt thereof for uses in treating cancer.

In some embodiments, the disclosure relates to a compound disclosed herein, or a pharmaceutically acceptable salt thereof, as defined herein for use in the treatment of cancer of the breast, colorectum, eye, lung (including small cell lung cancer, non-small cell lung cancer and bronchioalveolar cancer) and prostate.

In some embodiments, the disclosure relates to a compound disclosed herein, or a pharmaceutically acceptable salt thereof, as defined herein for use in the treatment of cancer of the bile duct, bone, bladder, eye, head and neck, kidney, liver, gastrointestinal tissue, esophagus, ovary, endometrium, pancreas, skin, testes, thyroid, uterus, cervix and vulva, and of leukemia (including ALL and CML), multiple myeloma and lymphomas.

In some embodiments, the disclosure relates to a compound disclosed herein, or a pharmaceutically acceptable salt thereof, as defined herein for use in the treatment of melanoma and tumors of the central nervous system and their metastases, and also for the treatment of glioblastomas.

Helbig et al. report a inhibitor of hypoxia-induced gene activation, improves local tumor control after fractionated irradiation in a schedule-dependent manner in head and neck human xenografts. Radiation Oncol, 2014, 9:207. In certain embodiments, the disclosure contemplates the treatment of squamous cell carcinoma, e.g., head and neck cancer using compounds disclosed herein.

Platz et al. report digoxin, a HIF inhibitor, as a possible drug for prostate cancer treatment. Cancer discovery, 2011, 2011(1):68-77. In certain embodiments, the disclosure contemplates the treatment of prostate cancer using compounds disclosed herein.

Wang et al. report down-regulation of hypoxia-inducible factor-1 suppresses malignant biological behavior of triple-negative breast cancer cells. Int J Clin Exp Med, 2014, 7(11):3933-40. In certain embodiments, the disclosure contemplates the treatment of breast cancer using compounds disclosed herein.

Niu et al. report LB-1 exerts antitumor activity in pancreatic cancer by inhibiting HIF-1α and Stat3 signaling. J Cell Physiol, 2015, doi: 10.1002/jcp.24949. In certain embodiments, the disclosure contemplates the treatment of pancreatic cancer using compounds disclosed herein.

Chen et al. report inhibition of hypoxia-induced angiogenesis via HIF-1 α/VEGF-A pathway in colorectal cancer. Alternat Med, 2015, 2015:454279. In certain embodiments, the disclosure contemplates the treatment of colorectal cancer using compounds disclosed herein.

Tang et al. report HIF-1α induces VE-cadherin expression and modulates vasculogenic mimicry in esophageal carcinoma cells. World J Gastroenterol, 2014, 20(47):17894-904. In certain embodiments, the disclosure contemplates the treatment of esophageal cancer using compounds disclosed herein.

Fisher et al. report panobinostat reduces hypoxia-induced cisplatin resistance of non-small cell lung carcinoma cells via HIF-1α destabilization. Mol Cancer, 2015, 14(1):4. In certain embodiments, the disclosure contemplates the treatment of lung cancer using compounds disclosed herein.

Chen et al. report HIF-α Promotes Chronic Myelogenous Leukemia Cell Proliferation by Upregulating p21 Expression. Cell Biochem Biophys. 2015. In certain embodiments, the disclosure contemplates the treatment of leukemia using compounds disclosed herein.

Womeldorff et al. report hypoxia-inducible factor-1 and associated upstream and downstream proteins in the pathophysiology and management of glioblastoma. Neurosurg Focus, 2014, 37(6):E8. In certain embodiments, the disclosure contemplates the treatment of glioblastoma using compounds disclosed herein.

Borsi et al., report therapeutic targeting of hypoxia and hypoxia-inducible factor 1 alpha in multiple myeloma. Transl Res, 2014, pii: S1931-5244(14)00436-8. In certain embodiments, the disclosure contemplates the treatment of myeloma using compounds disclosed herein.

Gao et al. report hispidulin inhibits proliferation and enhances chemosensitivity of gallbladder cancer cells by targeting HIF-1α. Exp Cell Res, 2014, pii: S0014-4827(14) 00524-2. In certain embodiments, the disclosure contemplates the treatment of gallbladder cancer using compounds disclosed herein.

In some embodiments, compounds disclosed herein could be used in the clinic either as a single agent by itself or in combination with other clinically relevant agents.

The anti-cancer treatment defined herein may be applied as a sole therapy or may involve, in addition to the compound of the disclosure, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites, nucleotide analogs, and nucleobase analogs (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon;

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin αvβ3 function and angiostatin);

(vi) vascular damaging agents such as Combretastatin A4;

(vii) antisense therapies, for example those which are directed to the targets listed above, such as an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Such conjoint treatment may be achieved by way of the simultaneous, sequential or separate dosing of the individual components of the treatment. Such combination products employ the compounds of this disclosure, or pharmaceutically acceptable salts thereof, within the dosage range described herein before and the other pharmaceutically-active agent within its approved dosage range.

Managing Other Conditions

Park et al. report HMGB1 induces angiogenesis in rheumatoid arthritis via HIF-1α activation. Eur J Immunol, 2014, doi: 10.1002/eji.201444908. In certain embodiments, the disclosure contemplates the treatment of rheumatoid arthritis using compounds disclosed herein.

Du et al. report Renalase is a target gene of hypoxia-inducible factor-1 in protection against cardiac ischemia-reperfusion injury. Cardiovasc Res, 2015, 105(2):182-91. In certain embodiments, the disclosure contemplates the treatment or prevention against myocardial ischemia-reperfusion injury or ischemic heart diseases such as hypertensive heart disease, coronary artery disease, cardiomyopathy, heart failure, myocardial infarction, cardiac dysrhythmias, endocarditis, inflammatory cardiomegaly, or myocarditis using compounds disclosed herein.

Mitochondrial Complex I Inhibitors as Pesticides

Rotenone is a broad-spectrum insecticide and pesticide. It occurs naturally in the seeds and stems of certain plants. Rotenone inhibits complex I activity. Thus, in certain embodiments, the disclosure contemplates the use of complex I inhibitors disclosed herein for uses as insecticides and pesticides. In certain embodiments, the disclosure relates to methods of contacting plants with complex I inhibitors disclosed herein to prevent pests from eating the plants. In certain embodiments, the disclosure contemplates contacting the plant by spraying crops, seeds, or soil with a solution or by dusting comprising complex I inhibitors disclosed herein. The complex I inhibitors prevent the pests such as insects from eating the plants due to the disrupting cellular respiration and killing or disabling the pest or insect.

Rotenone is also used in powdered form to treat scabies and lice, and parasitic mites on chickens and other livestock, and domestic pets. In certain embodiments, the disclosure contemplates treating or preventing pests from harboring in the skin or hair of a subject by contacting the skin or hair of the subject with complex I inhibitor disclosed herein in an effective manner in a subject at risk of, suspected of, exhibiting symptoms of or diagnosed with scabies, lice, parasites, or other pests.

In certain embodiments, the disclosure contemplates composition comprising complex I inhibitors disclosed herein in combination with other pesticides or insecticides such as organochlorides, DDT, organophosphates, pyrethroids, pyrethrum, neonicotinoids, nicotine, imidacloprid, ryanoids, ryanodine, chlorantraniliprole, insect growth regulators, diflubenzuron, juvenoids, methoprene, hydroprene, kinoprene, or tebufenozide.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids, which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier, which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as a prodrug can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing at least one compound according to the disclosure with one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of at least one compound of the disclosure, e.g., about 10, 25, 50, 100, 200, 300 or 400 mg per unit dosage.

The compounds can be administered by a variety of routes including oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers.

Certain of the above-mentioned polymers may further be crosslinked by way of standard techniques. The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

Experimental

Synthesis of Compounds

General procedure for SN2 displacement of bromide or tosyl group by alcohols: 1.0 equivalents of alcohol reagent was dissolved in anhydrous THF and cooled in an ice bath. 1.5 equivalents of NaH was added with stirring and after 30 minutes, 1.0 equivalents of corresponding electrophile was added and the reaction continued stirring overnight while warming to room temperature. The reaction was quenched with saturated NH₄Cl, taken up in ethyl acetate, washed with brined, dried over MgSO₄, and purified by flash column chromatography.

General procedure for coupling between aryl bromide and aryl aldehyde to form alcohols: 1.0 equivalents of aryl bromide was dissolved in anhydrous THF under argon and cooled in a dry ice/acetone bath. After 20 min, 1.4 equivalents of n-BuLi was added. After 20 min, 1.4 equivalents of aryl aldehyde was added. The reaction was stirred in the dry ice/acetone bath for 40 min before the reaction temperature was brought to room temperature and then quenched with saturated NH₄C₁. The reaction mixture was taken up in ethyl acetate, washed with brine, dried over MgSO₄, and purified by flash column chromatography. Exemplary characterization data for select compounds are below.

(3,4-Dimethoxyphenyl)(4-((((S)-tetrahydrofuran-3-yl)oxy)methyl)phenyl)methanol

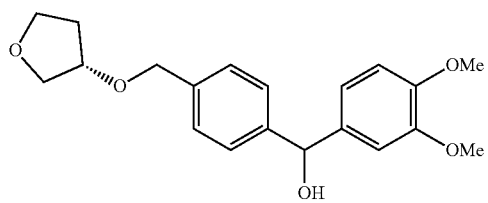 [SMILES: COc1ccc(C(O)c2ccc(CO[C@H]3CCOC3)cc2)cc1OC]

(3a). Yield: 94%. $^1$H NMR (400 MHz, CDCl$_3$): δ 7.26-7.24 (d, J=7.6 Hz, 2H), 7.19-7.17 (d, J=7.6 Hz, 2H), 6.83 (s, 1H), 6.76-6.74 (d, J=8.5 Hz, 1H), 6.69-6.67 (d, J=8.4 Hz, 1H), 5.58 (s, 1H), 4.35 (s, 2H), 4.06 (s, 1H), 3.73-3.60 (m, 10H), 1.91-1.81 (m, 2H) ppm. HRMS (ESI) m/z calculated for C$_{20}$H$_{23}$O$_5$ [(M−H)⁻] 343.1545, found 343.1532.

(4-(Butoxymethyl)phenyl)(3,4-dimethoxyphenyl)methanol (3i)

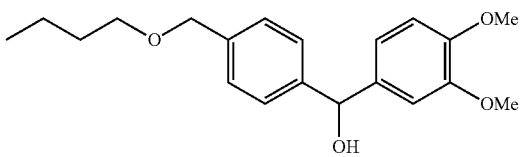 [SMILES: CCCCOCc1ccc(C(O)c2ccc(OC)c(OC)c2)cc1]

$^1$H NMR (400 MHz, CDCl$_3$): δ 7.34-7.32 (d, J=8 Hz, 2H), 7.30-7.28 (d, J=8.0 Hz, 2H), 6.90 (s,1H), 6.87-6.85 (d, J=8.0 Hz, 1H), 6.81-6.79 (d, J=8.0 Hz, 1H), 5.76 (s, 1H), 4.46 (s, 2H), 3.84 (s, 3H), 3.83 (s, 3H), 3.47-3.44 (t, J=6.0 Hz, 2H), 2.38 (s, 1H), 1.62-1.54 (m, 2H), 1.40-1.35 (m, 2H), 0.92-0.88 (t, J=8.0 Hz, 3H) ppm.

Tert-butyl 4-((3-((3,4-dimethoxyphenyl)(hydroxy)methyl)benzyl)oxy)piperidine-1-carboxylate (6b)

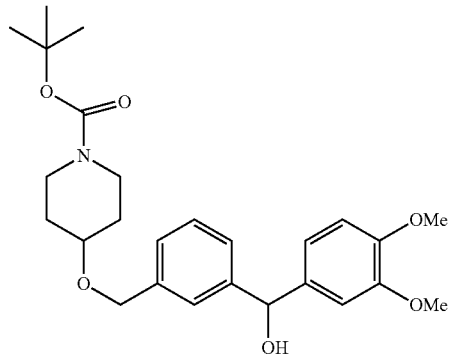 [SMILES: COc1ccc(C(O)c2cccc(COC3CCN(C(=O)OC(C)(C)C)CC3)c2)cc1OC]

$^1$H NMR (400 MHz, CDCl$_3$): δ 7.37 (s, 1H), 7.34-7.26 (m, 3H), 6.94 (s, 1H), 6.90-6.88 (d, J=8.0 Hz, 1H), 7.6.84-6.82 (d, J=8.0 Hz, 1H), 4.55 (s, 2H), 3.88 (s, 3H), 3.86 (s, 3H), 3.76 (m, 2H), 3.57-3.54 (m, 1H), 3.12-3.06 (m, 2H), 1.84 (m, 2H), 1.62-1.57 (m, 2H), 1.47 (s, 9H) ppm.

Tert-butyl 4-(2-(4-((3,4-dimethoxyphenyl)(hydroxy)methyl)-3-methylphenoxy)ethyl)piperidine-1-carboxylate (35e)

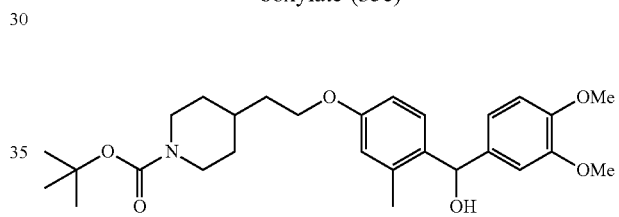

$^1$H NMR (400 MHz, CDCl$_3$) δ 7.37 (d, J=8.0 Hz, 1H), 6.92 (s, 1H), 6.83 (s, 2H), 6.80-6.68 (m, 2H), 5.94 (s, 1H), 4.32-4.11 (m, 2H), 4.02 (t, J=5.6 Hz, 2H), 3.88 (s, 3H), 3.86 (s, 3H), 2.75-2.71 (m, 2H), 2.27 (s, 3H), 2.03 (s, 1H), 1.75-1.71 (m, 5H), 1.48 (s, 9H), 1.26-1.12 (m, 2H) ppm.

Tert-butyl 4-(2-(4-(hydroxy(3,4,5-trimethoxyphenyl)methyl)-3-methylphenoxy)ethyl)piperidine-1-carboxylate (35g)

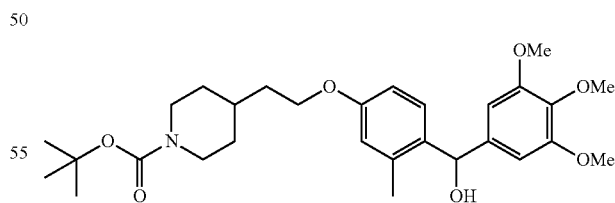

$^1$H NMR (400 MHz, CDCl$_3$) δ 7.29 (d, J=8.0 Hz, 1H), 6.75-6.72 (m, 2H), 6.58 (s, 2H), 5.90 (s, 1H), 4.17-4.03 (m, 2H), 3.99 (t, J=5.6 Hz, 2H), 3.83 (s, 3H), 3.81 (s, 6H), 2.76-2.66 (m, 2H), 2.30 (s, 3H), 2.11 (s, 1H), 1.75-1.69 (m, 5H), 1.45 (s, 9H), 1.23-1.09 (m, 2H) ppm.

Inhibition of Hypoxia-Inducible Gene Expression Driven by Exogenous HRE-Reporter Constructs in Glioma Cells LN229HRE-luc/lacZ cells were generated by stably transfecting human LN229 glioma cells with a bidirectional reporter construct (pBIGL-V6R) in which the firefly luciferase and LacZ reporter genes are under the control of 6 head to tail tandem copies of the VEGF HRE (hypoxia-responsive element—endogenous HIF-1 target gene) in rightward orientation (clone LN229V6R#18; Hygro selection 600 mg/mL) as reported in Yin et al. Clinical Cancer Research, 2012, 1-11.

Cells were pretreated with different doses of test compounds or 1% DMSO (final concentration in media) vehicle control for 1 hour under normoxia (21% $O_2$); then incubation continued under normoxia or hypoxia (1% $O_2$) using a hypoxia incubator (Thermo Forma model 3130). Firefly luciferase activities in lysates of LN229HRE-luc/LacZ cells were measured with a Dual-Luciferase Reporter Assay System (Promega) in a 20/20 n Luminometer (Promega). The $IC_{50}$ (µM) value for each individual compound was established from the dose-response curves.

| Scheme Name | Structure | IC50 |
|---|---|---|
| 3a | 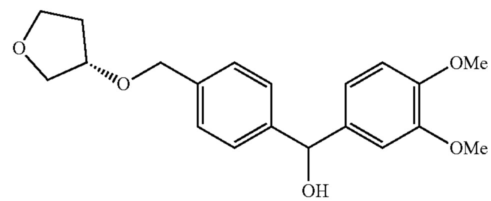 [SMILES: COc1ccc(C(O)c2ccc(CO[C@H]3CCOC3)cc2)cc1OC] | 0.3 |
| 3b | 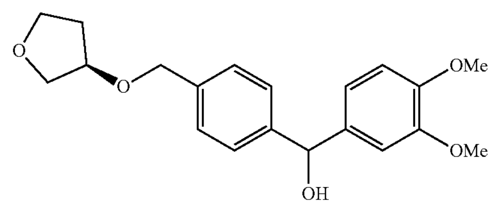 [SMILES: COc1ccc(C(O)c2ccc(CO[C@@H]3CCOC3)cc2)cc1OC] | 3.4 |
| 3c | 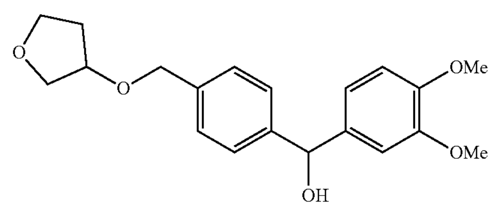 [SMILES: COc1ccc(C(O)c2ccc(COC3CCOC3)cc2)cc1OC] | 3.4 |
| 3d | 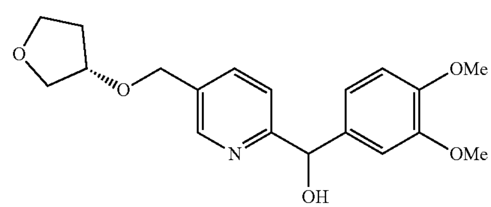 [SMILES: COc1ccc(C(O)c2ccc(CO[C@H]3CCOC3)cn2)cc1OC] | >5 |
| 3e | 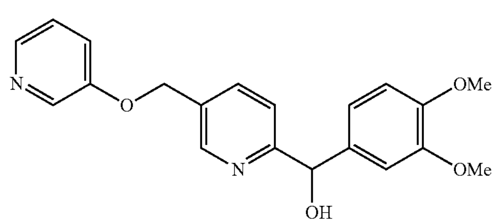 [SMILES: COc1ccc(C(O)c2ccc(COc3cccnc3)cn2)cc1OC] | >5 |
| 3f | 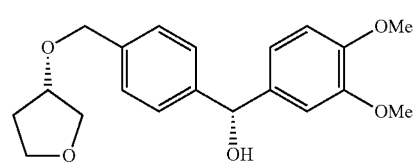 | >5 |

-continued
| Scheme Name | Structure | IC50 |
|---|---|---|
| 3g | 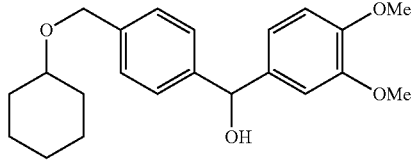 [SMILES: COc1ccc(C(O)c2ccc(COC3CCCCC3)cc2)cc1OC] | 0.4 |
| 3h | 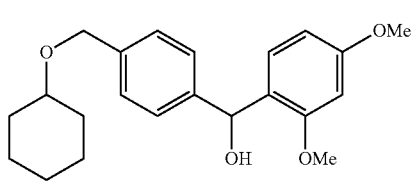 [SMILES: COc1ccc(C(O)c2ccc(COC3CCCCC3)cc2)c(OC)c1] | 0.68 |
| 3i | 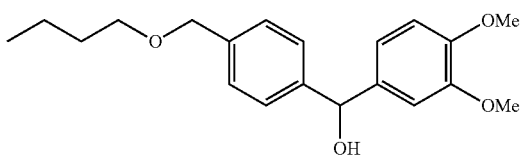 [SMILES: CCCCOCc1ccc(C(O)c2ccc(OC)c(OC)c2)cc1] | 0.5 |
| 3j | 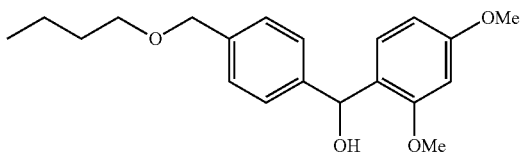 [SMILES: CCCCOCc1ccc(C(O)c2ccc(OC)cc2OC)cc1] | 0.63 |
| 3k | 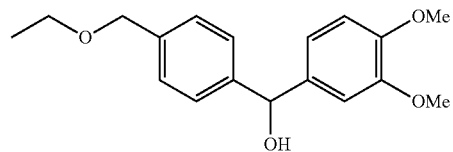 [SMILES: CCOCc1ccc(C(O)c2ccc(OC)c(OC)c2)cc1] | >5 |
| 3l | 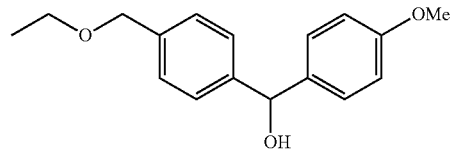 [SMILES: CCOCc1ccc(C(O)c2ccc(OC)cc2)cc1] | >5 |
| 3m | 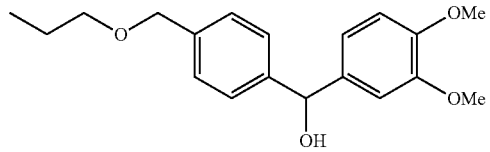 [SMILES: CCCOCc1ccc(C(O)c2ccc(OC)c(OC)c2)cc1] | 0.3 |
| 3n | 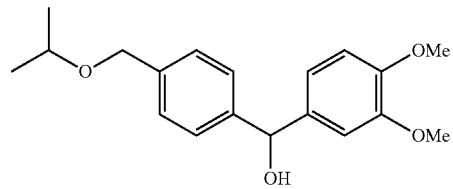 [SMILES: COc1ccc(C(O)c2ccc(COC(C)C)cc2)cc1OC] | >5 |
| 3o | 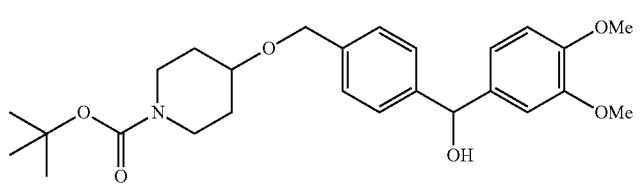 [SMILES: COc1ccc(C(O)c2ccc(COC3CCN(C(=O)OC(C)(C)C)CC3)cc2)cc1OC] | 0.89 |

-continued

| Scheme Name | Structure | IC50 |
|---|---|---|
| 3p | 4-(propoxymethyl)phenyl-(3-benzyloxy-4-methoxyphenyl)methanol | >5 |
| 3q | 4-(butoxymethyl)phenyl-(3-benzyloxyphenyl)methanol | >5 |
| 3r | 4-(propoxymethyl)phenyl-(4-(methoxymethoxy)phenyl)methanol | >5 |
| 3s | (4-((1-Boc-azetidin-3-yloxy)methyl)phenyl)-(3,4-dimethoxyphenyl)methanol | >5 |
| 3t | (4-(((S)-1-Boc-pyrrolidin-3-yloxy)methyl)phenyl)-(3,4-dimethoxyphenyl)methanol | >5 |
| 3u | 4-(propoxymethyl)phenyl-(3-(methoxymethoxy)-4-methoxyphenyl)methanol | >5 |
| 3v | 4-(propoxymethyl)phenyl-(4-methoxy-3-propoxyphenyl)methanol | 5 |

-continued
| Scheme Name | Structure | IC50 |
|---|---|---|
| 3w | 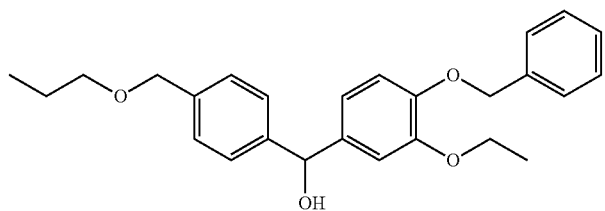 [SMILES: CCCOCc1ccc(C(O)c2ccc(OCc3ccccc3)c(OCC)c2)cc1] | >5 |
| 6a | 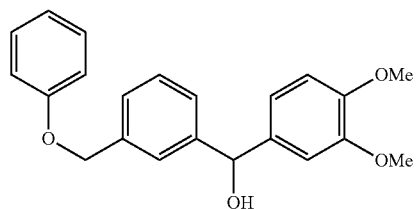 [SMILES: COc1ccc(C(O)c2cccc(COc3ccccc3)c2)cc1OC] | 1.0 |
| 6b | 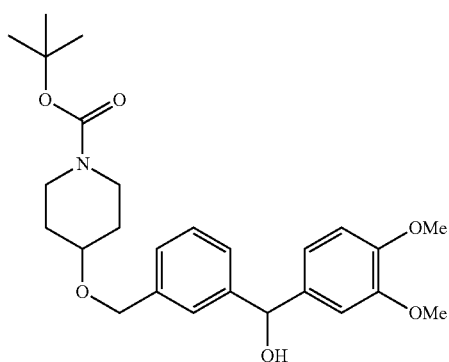 [SMILES: COc1ccc(C(O)c2cccc(COC3CCN(C(=O)OC(C)(C)C)CC3)c2)cc1OC] | 0.2 |
| 6c | 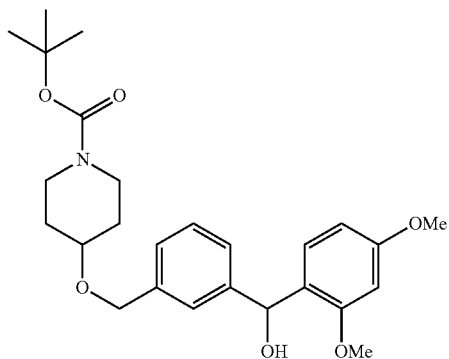 [SMILES: COc1ccc(C(O)c2cccc(COC3CCN(C(=O)OC(C)(C)C)CC3)c2)c(OC)c1] | 0.55 |
| 6d | 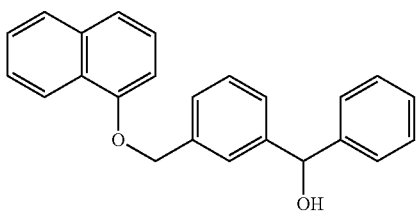 [SMILES: OC(c1ccccc1)c1cccc(COc2cccc3ccccc23)c1] | >5 |

| Scheme Name | Structure | IC50 |
|---|---|---|
| 6e | 1-naphthyloxymethyl-phenyl-(3,4-dimethoxyphenyl)methanol | 1.83 |
| 6f | (3-(ethoxymethyl)phenyl)(4-methoxyphenyl)methanol | >5 |
| 6g | (3-(butoxymethyl)phenyl)(4-methoxyphenyl)methanol | >5 |
| 6h | (3-(butoxymethyl)phenyl)(2,4-dimethoxyphenyl)methanol | 0.48 |
| 6i | (3-(propoxymethyl)phenyl)(2,4-dimethoxyphenyl)methanol | 5 |
| 6j | (3-(butoxymethyl)phenyl)(3,4-dimethoxyphenyl)methanol | 2.45 |
| 6k | (3-(propoxymethyl)phenyl)(3-butoxyphenyl)methanol | 3.8 |
| 6l | (3-(butoxymethyl)phenyl)(3-(benzyloxy)-4-methoxyphenyl)methanol | 2.98 |
| 6m | (3-(butoxymethyl)phenyl)(3-(benzyloxy)phenyl)methanol | >5 |

-continued

| Scheme Name | Structure | IC50 |
|---|---|---|
| 6n | 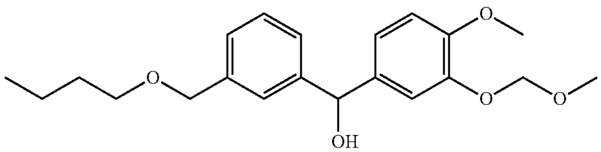 [SMILES: CCCCOCc1cccc(C(O)c2ccc(OC)c(OCOC)c2)c1] | 0.75 |
| 6o | 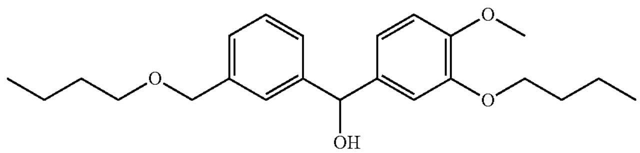 [SMILES: CCCCOCc1cccc(C(O)c2ccc(OC)c(OCCCC)c2)c1] | 1.0 |
| 6p | 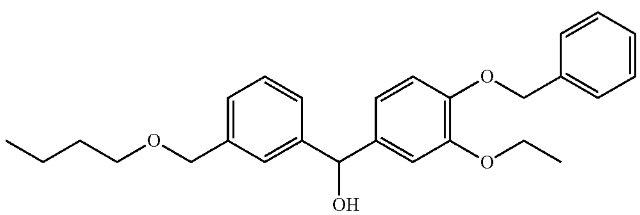 [SMILES: CCCCOCc1cccc(C(O)c2ccc(OCc3ccccc3)c(OCC)c2)c1] | 0.62 |
| 9a | 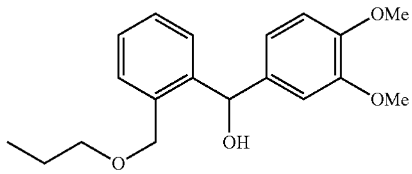 [SMILES: CCCOCc1ccccc1C(O)c1ccc(OC)c(OC)c1] | >5 |
| 9b | 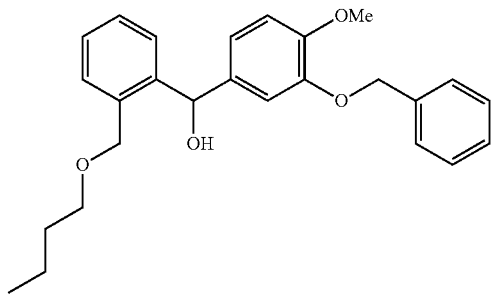 [SMILES: CCCCOCc1ccccc1C(O)c1ccc(OC)c(OCc2ccccc2)c1] | >5 |
| 9c | 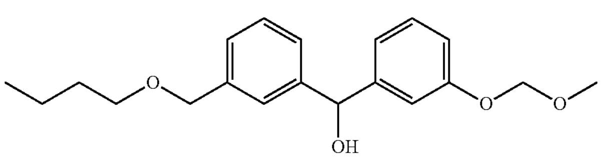 [SMILES: CCCCOCc1cccc(C(O)c2cccc(OCOC)c2)c1] | >5 |
| 9d | 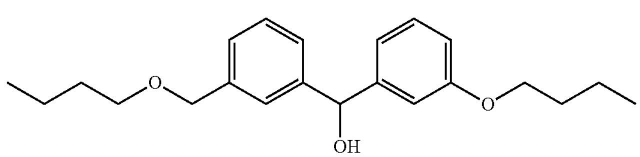 [SMILES: CCCCOCc1cccc(C(O)c2cccc(OCCCC)c2)c1] | >5 |
| 14a | 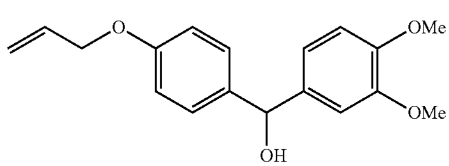 [SMILES: C=CCOc1ccc(C(O)c2ccc(OC)c(OC)c2)cc1] | >5 |

-continued

| Scheme Name | Structure | IC50 |
|---|---|---|
| 14b | (4-pentyloxyphenyl)(3,4-dimethoxyphenyl)methanol | 1.9 |
| 14c | (4-(2-(1-Boc-piperidin-4-yl)ethoxy)phenyl)(3,4-dimethoxyphenyl)methanol | 0.33 |
| 15a | (5-butoxypyridin-2-yl)(3,4-dimethoxyphenyl)methanol | >5 |
| 15b | (5-butoxypyridin-2-yl)(2,4-dimethoxyphenyl)methanol | >5 |
| 15c | (5-isopropoxypyridin-2-yl)(3,4-dimethoxyphenyl)methanol | >5 |
| 15d | (5-isopropoxypyridin-2-yl)(2,4-dimethoxyphenyl)methanol | >5 |
| 14d | (5-(oxazol-5-ylmethoxy)pyridin-2-yl)(3,4-dimethoxyphenyl)methanol | >5 |
| 21a | (5-(morpholinomethyl)pyridin-2-yl)(3,4-dimethoxyphenyl)methanol | >5 |
| 21b | (4-((4-Boc-piperazin-1-yl)methyl)phenyl)(3,4-dimethoxyphenyl)methanol | 1.49 |

-continued

| Scheme Name | Structure | IC50 |
|---|---|---|
| 21c | 4-(bromomethyl)phenyl-(3,4-dimethoxyphenyl)methanol | 1.0 |
| 24a | phenyl-(3,4-dimethoxyphenyl)methanol | 2.2 |
| 24b | (3,4-dimethoxyphenyl)-(3,4-dimethoxyphenyl)methanol | >5 |
| 24c | (2,5-dimethoxyphenyl)-(3,4-dimethoxyphenyl)methanol | >5 |
| 24d | [4-(4-methylpiperazin-1-yl)phenyl]-(3,4-dimethoxyphenyl)methanol | >5 |
| 24e | [4-(tetrahydrofuran-2-yl)phenyl]-(3,4-dimethoxyphenyl)methanol | 5 |
| 24f | biphenyl-4-yl-(3,4-dimethoxyphenyl)methanol | >5 |
| 26a | (2,2-dimethyl-2H-chromen-6-yl)-(3,4-dimethoxyphenyl)methanol | 0.6 |

-continued

| Scheme Name | Structure | IC50 |
|---|---|---|
| 26b | 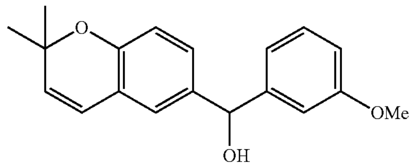 [SMILES: COc1cccc(C(O)c2ccc3c(c2)C=CC(C)(C)O3)c1] | >5 |
| 26c | 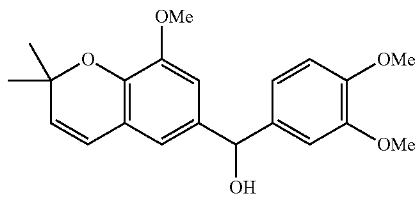 [SMILES: COc1ccc(C(O)c2cc3c(c(OC)c2)OC(C)(C)C=C3)cc1OC] | 3.1 |
| 26d | 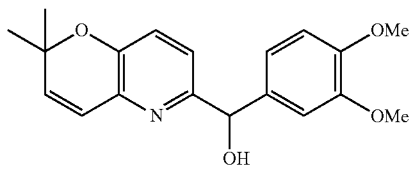 [SMILES: COc1ccc(C(O)c2ccc3c(n2)C=CC(C)(C)O3)cc1OC] | 2.25 |
| 27c | 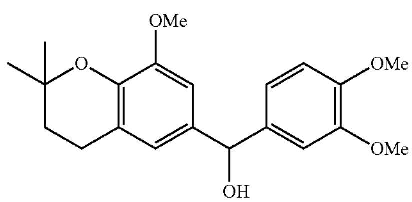 [SMILES: COc1ccc(C(O)c2cc3c(c(OC)c2)OC(C)(C)CC3)cc1OC] | 4.2 |
| 27d | 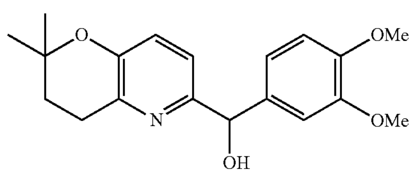 [SMILES: COc1ccc(C(O)c2ccc3c(n2)CCC(C)(C)O3)cc1OC] | 2.3 |
| 29a | 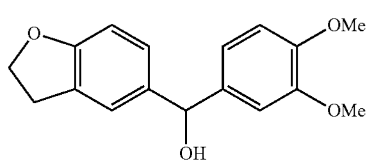 [SMILES: COc1ccc(C(O)c2ccc3c(c2)CCO3)cc1OC] | >5 |
| 29b | 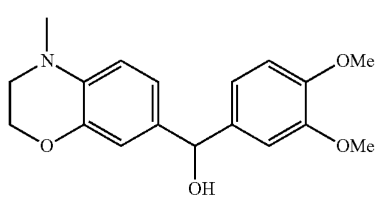 [SMILES: COc1ccc(C(O)c2ccc3c(c2)OCCN3C)cc1OC] | >5 |
| 29c | 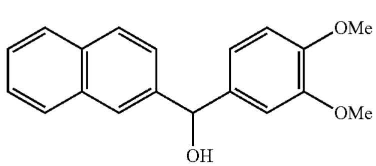 [SMILES: COc1ccc(C(O)c2ccc3ccccc3c2)cc1OC] | 1.2 |

| Scheme Name | Structure | IC50 |
|---|---|---|
| 29d | 2,3-dihydrobenzo[b][1,4]dioxin-6-yl(3,4-dimethoxyphenyl)methanol | 4.18 |
| 29e | (2-methylbenzo[b]thiophen-5-yl)(3,4-dimethoxyphenyl)methanol | 1.03 |
| 29f | (2-methylbenzo[b]thiophen-5-yl)(2,4-dimethoxyphenyl)methanol | >5 |
| 32a | (6-(hexyloxy)naphthalen-2-yl)(3,4-dimethoxyphenyl)methanol | 1.8 |
| 32b | (6-propoxynaphthalen-2-yl)(3,4-dimethoxyphenyl)methanol | 2.95 |
| 32c | (6-butoxynaphthalen-2-yl)(3,4-dimethoxyphenyl)methanol | 3.33 |
| 32d | (6-isopropoxynaphthalen-2-yl)(3,4-dimethoxyphenyl)methanol | 2.62 |
| 35a | (2-methoxy-4-((tetrahydrofuran-3-yl)oxy)phenyl)(3,4-dimethoxyphenyl)methanol | 4.2 |
| 35b | (2-fluoro-4-(pentyloxy)phenyl)(3,4-dimethoxyphenyl)methanol | 1.3 |

-continued
| Scheme Name | Structure | IC50 |
|---|---|---|
| 35c | 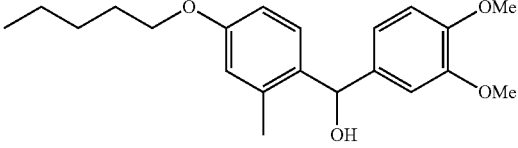 [SMILES: CCCCCOc1ccc(C(O)c2ccc(OC)c(OC)c2)c(C)c1] | 0.43 |
| 35d | 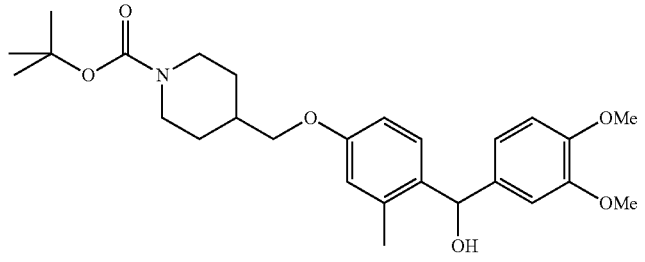 [SMILES: COc1ccc(C(O)c2ccc(OCC3CCN(C(=O)OC(C)(C)C)CC3)cc2C)cc1OC] | 0.33 |
| 35e | 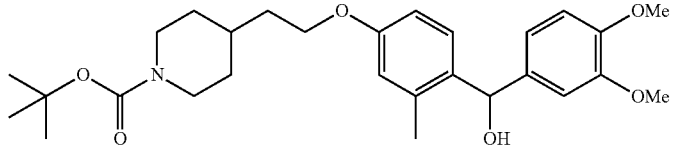 [SMILES: COc1ccc(C(O)c2ccc(OCCC3CCN(C(=O)OC(C)(C)C)CC3)cc2C)cc1OC] | 0.27 |
| 35f | 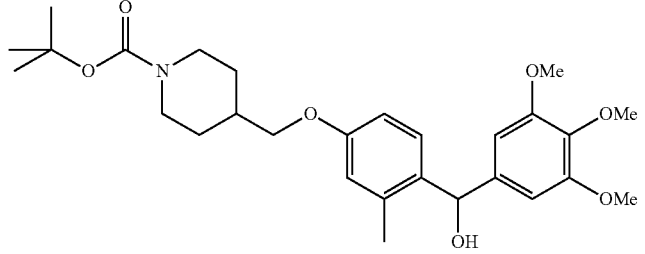 [SMILES: COc1cc(C(O)c2ccc(OCC3CCN(C(=O)OC(C)(C)C)CC3)cc2C)cc(OC)c1OC] | 0.27 |
| 35g | 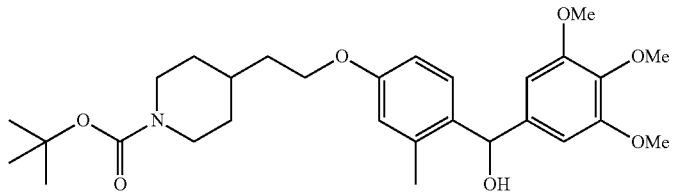 [SMILES: COc1cc(C(O)c2ccc(OCCC3CCN(C(=O)OC(C)(C)C)CC3)cc2C)cc(OC)c1OC] | 0.27 |
| 36c | 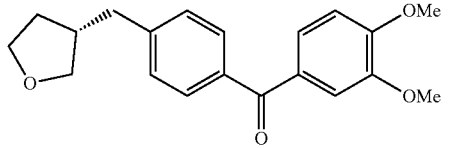 [SMILES: COc1ccc(C(=O)c2ccc(C[C@H]3CCOC3)cc2)cc1OC] | >5 |
| 36d | 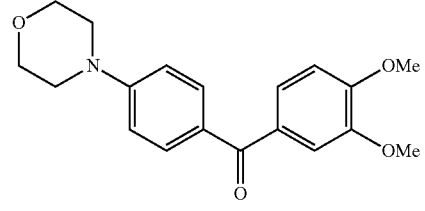 [SMILES: COc1ccc(C(=O)c2ccc(N3CCOCC3)cc2)cc1OC] | >5 |

| Scheme Name | Structure | IC50 |
|---|---|---|
| 36e | 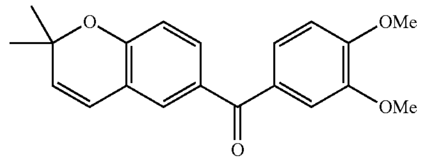 [SMILES: COc1ccc(C(=O)c2ccc3c(c2)C=CC(C)(C)O3)cc1OC] | >5 |
| 36f | 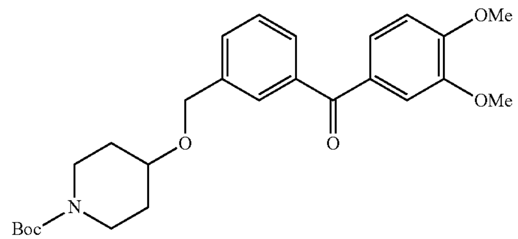 [SMILES: COc1ccc(C(=O)c2cccc(COC3CCN(C(=O)OC(C)(C)C)CC3)c2)cc1OC] | >5 |
| 36g | 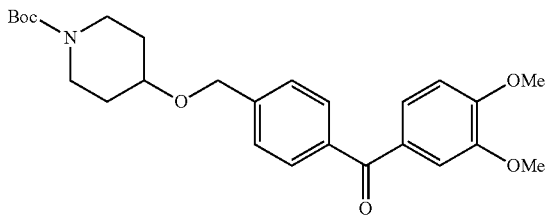 [SMILES: COc1ccc(C(=O)c2ccc(COC3CCN(C(=O)OC(C)(C)C)CC3)cc2)cc1OC] | 4.5 |
| 36h | 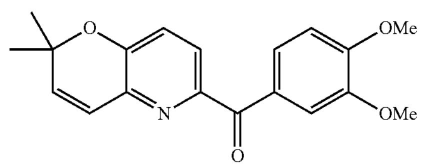 [SMILES: COc1ccc(C(=O)c2ccc3c(n2)C=CC(C)(C)O3)cc1OC] | >5 |

Mitochondrial Inhibition

Complex I (NADH:ubiquinone oxidoreductase or NADH dehydrogenase (ubiquinone)) is a complex of enzymes of the respiratory chains that catalyzes the transfer of electrons from NADH to coenzyme Q10 (CoQ10) located in the inner mitochondrial membrane. Ellinghaus et al. report that BAY 87-2243 inhibits HIF-1α. Cancer Medicine, 2013, 2(5): 611-624. Antitumor activity of BAY 87-2243 in vivo was demonstrated in a H460 xenograft model. BAY 87-2243 also inhibits mitochondrial complex I activity. Interference with mitochondrial function to reduce hypoxia-induced HIF-1 activity in tumors is indicated as a therapeutic approach to overcome chemo- and radiotherapy resistance of hypoxic tumors. Helbig et al. report BAY 87-2243 improves local tumor control after fractionated irradiation in a schedule-dependent manner in head and neck human xenografts. Radiation Oncology 2014, 9:207. Santidrian et al. report mitochondrial complex I activity and NAD+/NADH balance regulate breast cancer progression. J Clin Invest, 2013, 123(3):1068-81. See also Ellinghaus et al., Cancer Med, 2013, 2(5):611-624. Chang et al., Clin Cancer Res, 2015, 21(2):335-46; Fulda et al., Antioxid Redox Signal, 2011, 15:2937-2949; Wenner, J Cell Physiol, 2012, 227:450-456; Fulda et al., Nat Rev Drug Discov, 2010, 9:447-464.

Figure 9:
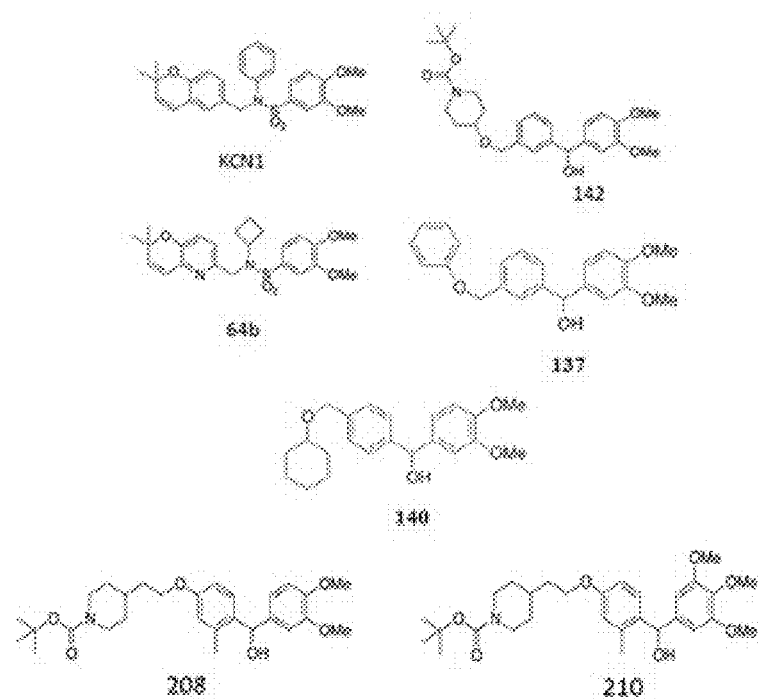
FIG. 9 illustrates the structure of certain HIF inhibitors.
Figure 10:
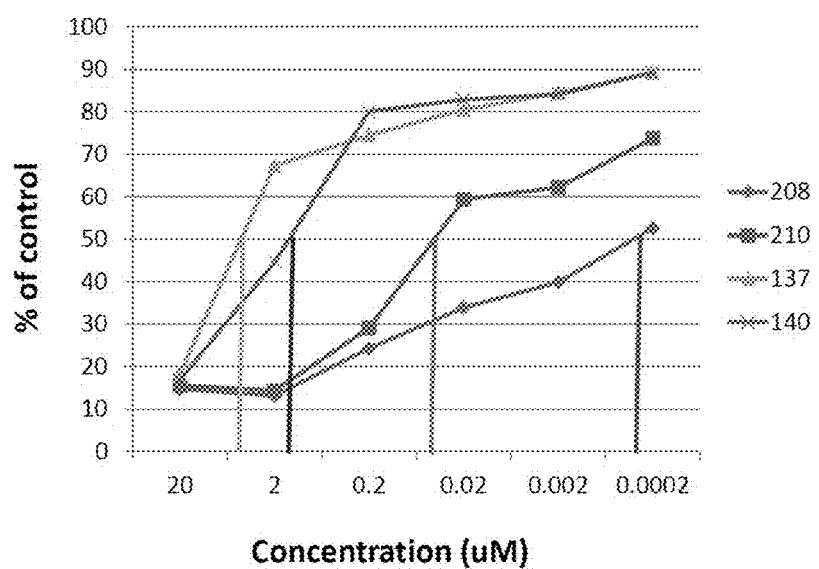
FIG. 10 shows the $IC_{50}$ of certain benzhydrols in Complex I activity assays (MitoCheck Complex I activity assay Cayman Chemicals #700930.
Figure 11:
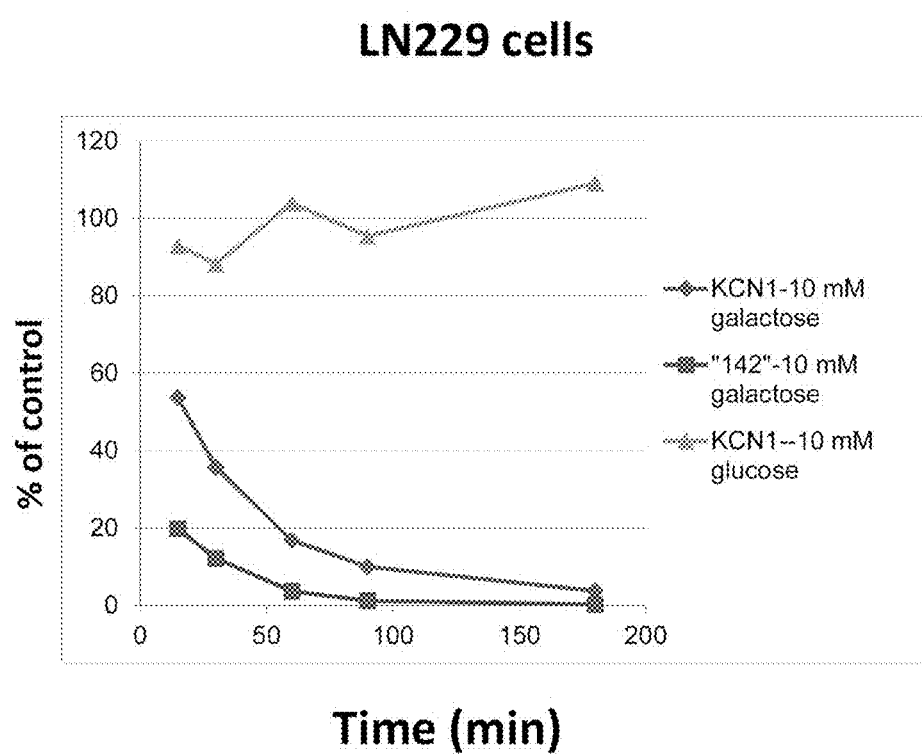
FIG. 11 shows data on the time course of effects of KCN1 and 142 on ATP production in galactose-containing media.

It has been discovered that certain HIF inhibitors disclosed herein are also mitochondrial inhibitors. The $IC_{50}$ of KCN1 in MitoCheck Complex I activity assay from Cayman Chemicals #700930 is about 15 μM, 64b is about 15 μM, compound 208 is about 0.5 nM, and compound 210 is about 40 nM. See FIGS. 9 and 10. KCN1 is a HIF inhibitor that strongly acidifies cell culture media due to increased lactate production thought to be due to glucose consumption. KCN1 induced acidification of media may be due to the consequence of its mitochondrial inhibiting activity. Inhibiting the mitochondrial complex I interferes with the normal functions of the electron transport chain. This in effect can damage DNA and specific components of the mitochondria which leads to cell death through the generation of reactive oxygen species.

To be metabolized, galactose has to be converted into glucose in an energy consuming process that cannot be balanced by glycolytic metabolism. Hence, cells grown in galactose rely mostly on oxidative phosphorylation to produce ATP and are more sensitive to mitochondrial inhibitors than cells grown in high glucose medium. KCN1 is toxic to LN229 cells in the presence of galactose. This data indicates that it may be beneficial to feed subjects a glucose-free diet (galactose or ketogenic diet) in combination with mitochondrial complex I inhibitors disclosed herein. Thus, in certain embodiments, the disclosure contemplates administering compounds disclosed herein in combination with a restricted or low glucose diet optionally in combination with galactose.

What is claimed is:

1. A compound having Formula I

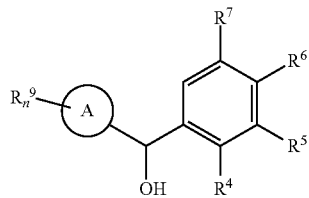

Formula I or pharmaceutically acceptable salts thereof, wherein:
A is an aryl ring;
n is 1, 2, or 3;
$R^4$ and $R^7$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl;
$R^5$ and $R^6$ are each alkoxy;
$R^9$ is alkoxy substituted with $R^{20}$;
$R^{20}$ is carbocyclyl, aryl, or heterocyclyl, wherein $R^{20}$ is substituted with one or more, the same or different, $R^{21}$; and
$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound according to claim 1, wherein A is phenyl.

3. The compound according to claim 1, wherein $R^9$ is (2-piperidin-4-yl)ethoxy or (2-(N-alkoxycarbonyl)piperidin-4-yl)ethoxy.

4. A compound having Formula II

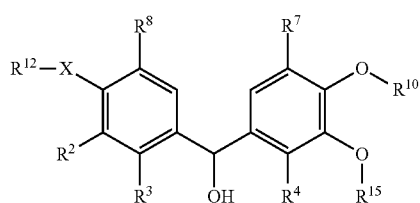

Formula II or pharmaceutically acceptable salts thereof wherein,
X is —CH$_2$O— or —CH$_2$CH$_2$O—;
$R^{12}$ is carbocyclyl, aryl, or heterocyclyl, wherein $R^{12}$ is substituted with one or more, the same or different, $R^{20}$;
$R^{20}$ is alkyl, halogen, nitro, cyano, hydroxy, amino, mercapto, formyl, carboxy, carbamoyl, hydroxyalkyl, alkoxy, thioalkyl, alkylthio, aminoalkyl, alkylamino, (alkyl)$_2$amino, alkanoyl, alkoxycarbonyl, alkylsulfinyl, alkylsulfonyl, arylsulfonyl, carbocyclyl, aryl, or heterocyclyl, wherein $R^{20}$ is optionally substituted with one or more, the same or different, $R^{21}$;
$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$R^2$ is hydrogen, alkyl, halogen, or alkoxy;
$R^3$ is hydrogen, alkyl, halogen, or alkoxy;
$R^4$, $R^7$, and $R^8$ are each hydrogen;
$R^{10}$ is alkyl, formyl, alkanoyl, carbamoyl, hydroxyalkyl, aminoalkyl, or thioalkyl wherein $R^{10}$ is optionally substituted with one or more, the same or different, $R^{20}$; and
$R^{15}$ is alkyl, formyl, alkanoyl, carbamoyl, hydroxyalkyl, aminoalkyl, or thioalkyl wherein $R^5$ is optionally substituted with one or more, the same or different, $R^{20}$.

5. The compound according to claim 4, wherein X is —CH$_2$CH$_2$O—.

6. The compound according to claim 5, wherein $R^{12}$ is heterocyclyl.

7. The compound according to claim 1, selected from the group consisting of
tert-butyl 4-(2-(4-(hydroxy(3,4-dimethoxyphenyl)methyl)-3-methylphenoxy)ethyl)piperidine-1-carboxylate; and
tert-butyl 4-(2-(4-(hydroxy(3, 4,5-trimethoxyphenyl)methyl)-3-methylphenoxy)ethyl)piperidine-1-carboxylate.

8. A pharmaceutical composition, comprising a compound according to claim 1, or a pharmaceutically acceptable salt and a pharmaceutically acceptable excipient.

9. The compound according to claim 1, wherein $R^9$ is ((piperidin-4-yl)oxy)methyl.

10. The compound according to claim 1, wherein the compound is tert-butyl 4-(2-(4-(hydroxy(3,4-dimethoxyphenyl)methyl)-3-methylphenoxy)ethyl)piperidine-1-carboxylate.

* * * * *

UNITED STATES PATENT AND TRADEMARK OFFICE
CERTIFICATE OF CORRECTION

PATENT NO.         : 10,772,858 B2                         Page 1 of 1
APPLICATION NO.    : 15/570969
DATED              : September 15, 2020
INVENTOR(S)        : Binghe Wang et al.

It is certified that error appears in the above-identified patent and that said Letters Patent is hereby corrected as shown below:

In the Claims

Column 52, Lines 37-38, Delete:
"...aminoalkyl, or thioalkyl wherein $R^5$ is optionally substituted with one or more, the same or different, $R^{20}$."

And Insert:
--...aminoalkyl, or thioalkyl wherein $R^{15}$ is optionally substituted with one or more, the same or different, $R^{20}$.--

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*